United States Patent
Ziegler et al.

(10) Patent No.: US 9,941,440 B2
(45) Date of Patent: *Apr. 10, 2018

(54) RADIATION MICRODOSIMETERS CORRELATED WITH BIOLOGICAL CELLS AND CELL COMPONENTS

(71) Applicants: James Francis Ziegler, Chester, MD (US); Chao-tuan Liu, Northridge, CA (US); Razmig Messerian, Pasadena, CA (US); Wayne Newhauser, Baton Rouge, LA (US)

(72) Inventors: James Francis Ziegler, Chester, MD (US); Chao-tuan Liu, Northridge, CA (US); Razmig Messerian, Pasadena, CA (US); Wayne Newhauser, Baton Rouge, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/836,888

(22) Filed: Aug. 26, 2015

(65) Prior Publication Data
US 2015/0372182 A1 Dec. 24, 2015

Related U.S. Application Data

(63) Continuation of application No. 14/469,431, filed on Aug. 26, 2014, now abandoned, which is a (Continued)

(51) Int. Cl.
*G01N 27/00* (2006.01)
*H01L 27/14* (2006.01)
(Continued)

(52) U.S. Cl.
CPC .............. *H01L 31/18* (2013.01); *G01N 23/00* (2013.01); *G01N 23/10* (2013.01);
(Continued)

(58) Field of Classification Search
CPC .......... G01N 33/0031; G01N 33/0032; G01N 23/00; G01N 23/08; G01T 1/16; G01T 1/24; G01T 1/241; G01T 1/243
USPC .................. 250/370.01, 370.07; 422/98, 502
See application file for complete search history.

(56) References Cited

U.S. PATENT DOCUMENTS 5,256,879 A * 10/1993 McNulty ................. G01T 1/247
250/370.06
5,596,199 A    1/1997 McNulty et al.
(Continued)

OTHER PUBLICATIONS

Davis et al., "Tissue equivalency of diamond for proton and alpha particles typical of Galactic Cosmic Rays", 2012.
(Continued)

*Primary Examiner* — Jill Warden
*Assistant Examiner* — Dwayne K Handy
(74) *Attorney, Agent, or Firm* — Loza & Loza LLP; Razmig Messerian

(57) ABSTRACT

One feature pertains to a radiation dosimeter comprising a microdosimeter cell array that includes a first microdosimeter cell having a first semiconductor volume configured to generate a first current in response to incident radiation. The first semiconductor volume may have at least one of a first size, a first shape, a first semiconductor type, and/or a first semiconductor doping type and concentration that is associated with a first biological cell type or a first biological cell component type. The dosimeter may further comprise a processing circuit communicatively coupled to the microdosimeter cell array and configured to generate a signal based on the first current. The signal generated may be indicative of an amount of radiation absorbed by the microdosimeter cell array. A display may be utilized by the dosimeter to show a radiation level reading based on the signal generated.

20 Claims, 19 Drawing Sheets

Related U.S. Application Data continuation of application No. 13/959,616, filed on Aug. 5, 2013, now Pat. No. 8,858,888.

(60) Provisional application No. 61/739,580, filed on Dec. 19, 2012.

(51) Int. Cl.

| | | |
|---|---|---|
| *H01L 31/18* | (2006.01) | |
| *G01T 1/02* | (2006.01) | |
| *G01N 23/00* | (2006.01) | |
| *G01N 23/10* | (2018.01) | |
| *G01N 33/487* | (2006.01) | |
| *H01L 27/146* | (2006.01) | |
| *A61B 6/00* | (2006.01) | |

(52) U.S. Cl.
CPC ....... *G01N 33/48728* (2013.01); *G01T 1/026* (2013.01); *H01L 27/14683* (2013.01); *A61B 6/42* (2013.01); *A61B 6/542* (2013.01)

(56) References Cited

U.S. PATENT DOCUMENTS

| | | |
|---|---|---|
| 6,278,117 B1 | 8/2001 | Bardash |
| 7,500,746 B1 | 3/2009 | Howell et al. |
| 8,350,225 B1 | 1/2013 | Bardash |
| 8,421,022 B2 | 4/2013 | Rozenfeld |
| 8,858,888 B2 * | 10/2014 | Ziegler ............... G01N 23/00 250/370.01 |
| 2006/0027756 A1 | 2/2006 | Thomson et al. |
| 2010/0090118 A1 | 4/2010 | Rozenfeld |

OTHER PUBLICATIONS

Livingstone et al., "Comparison of Epitaxial and SOI based Large Area Microdosimeters", Submitted to 2011 IEEE Nuclear Science Symposium and Medical Imaging Conference, Valencia, Spain, Oct. 23-29, 2011.(to be published in Engineering and Physical Sciences in Medicine (ESPM).

Prokopovich et al., "Comparison of SOI Microdosimeter and Tissue Equivalent Proportional Counter Measurements at the CERF Facility", IEEE Trans. on Nucl. Sci., NS-59, 2351-2354, 2012.

Rosenfeld, "Advanced Semiconductor Dosimetry in Radiation Therapy", AIP Conference Proceedings, vol. 1345, "Concepts and Trends in Medical Radiation Dosimetry", 2011.

Van Dam et al., "ESTRO Booklet on Physics for Clinical Radiotherapy No. 1", (Garant, Leuven-Apeldoorn, 1994).

Ziegler et al., "SRIM—The Stopping and Range of Ions in Matter (2010)", Nuclear Inst. and Meth., vol. B-268, 1818-1823 (2010).

* cited by examiner

1800

| Biological Cell Type | Relative Radiation Sensitivity Scaling Factor (RRSSF) |
|---|---|
| Neutrophil Cell | 0.25 |
| Cortical Bone Cell | 0.05 |
| Skeletal Muscle Cell | 0.06 |
| Epithelial Colon Cell | 0.28 |

| Biological Cell Component Type | Relative Radiation Sensitivity Scaling Factor (RRSSF) |
|---|---|
| Mitochondrion | 0.10 |
| Golgi Apparatus | 0.08 |
| Nucleus | 0.40 |
| Specific Granule | 0.03 |

*FIG. 19*

RADIATION MICRODOSIMETERS CORRELATED WITH BIOLOGICAL CELLS AND CELL COMPONENTS

CLAIM OF PRIORITY

The present application for patent is a continuation application of U.S. patent application Ser. No. 14/469,431 entitled "Radiation Microdosimeters Correlated with Biological Cells and Cell Components" filed Aug. 26, 2014, which is a continuation of U.S. patent application Ser. No. 13/959,616, now U.S. Pat. No. 8,858,888 entitled "Radiation Microdosimeters Correlated with Biological Cells and Cell Components" filed Aug. 5, 2013, which in turn claims priority to provisional application No. 61/739,580 entitled "Radiation Microdosimeter Correlated with Tissue Structures" filed Dec. 19, 2012, the entire disclosures of which are hereby expressly incorporated by reference.

BACKGROUND

Field

Various features relate to radiation microdosimeters, and more specifically, to solid state microdosimeters that correlate to biological tissue structures.

Background

Classical radiation absorbed dosimetry operates to determine the average energy deposited per unit mass, J/kg, but cannot predict the radiobiological effects in biological tissue for the detected radiation. Early attempts at understanding radiation effects on tissue recognized that knowledge of the energy distribution at a scale comparable to the structures affected by irradiation was essential, and hence knowledge of the energy distribution at the cellular level and even DNA level. Consequently, the study of radiation effects on living cells or cell components is called "microdosimetry."

One of the factors affecting local energy deposition is termed "Linear Energy Transfer" (LET). LET is the linear density of energy lost by an ionizing particle travelling through matter. For example, it may be the loss of energy per unit distance along the path of radiation, especially the path of charged particles. With micro-sized targets, deterministic energy deposition becomes stochastic and depends on the target size and spatial pattern of energy deposited by ionizing radiation (e.g., charged particles). It limits the correlation of the LET approach with radiobiological effects.

There are several reasons for the limitations in the LET concept. First, the delta ray distribution and its relationship to spatial dose distributions are not adequately accounted for in most analyses. Also, particles with different velocities and charges can have the same LET but the particle velocity largely determines the energy distribution of delta rays. In microscopic volumes, the delta ray distribution may be a significant factor in the spatial distribution of energy, particularly at higher particle energies and smaller target tissue sizes. Further, LET is a non-stochastic average quantity, and it does not account for the random fluctuations in energy deposition which manifests as the clustering of energy deposition and range straggling of radiation particles. This variance due to straggling may exceed the path length variations at high particle energies and smaller tissue sizes.

These limitations in LET lead to the formulation of a set of measurable stochastic quantities, which produce the fundamental basis for the field of microdosimetry. Microdosimetry requires instrumentation for measurements of energy deposited in a cellular size or smaller. Instruments to approximate such measurements were developed in the 1940's, such as the low pressure gas proportional counter, also referred to as the "Rossi" counter. This dosimeter is still one of the most common radiation dosimeters, especially in a form known as a "Tissue-Equivalent Proportional Counter" (TEPC). A TEPC uses low-pressure gases, usually of a type that mimics tissue equivalent compounds, and may be surrounded by similar tissue-equivalent materials.

TEPCs have several shortcomings. First, TEPCs require a gas supply system that is inconvenient in many portable applications. Second, TEPCs are relatively large (e.g., 1 cm or larger in diameter), which severely limits the spatial resolution of any detected radiation. Third, TEPCs require high voltages, for example, up to 2,000 volts or more is commonplace. As such, TEPCs are relatively power-hungry devices that cannot be used in a passive mode for weeks or months at a time, since a TEPC cannot record radiation events without power. Fourth, TEPCs suffer from the "wall effect" and other size-related problems since they are very large compared to tissue cells and tissue cell components. This leads to artifacts in the analysis of their microdosimetry spectra. Finally, and most notably, very large volume correction factors are required to compensate for the difference between the TEPC volume (i.e., testing space volume used by the TEPC) and a tissue structure volume (e.g., cell volume) that the TEPC is being used to estimate the radiation energy deposited within. Such a correction factor may be, for example, of the order of 18,000 times or more.

Microdosimetric spectra can be converted to radiobiological characteristics of the radiation field by convolution with a quality coefficient Q over the range of lineal deposited energies, which reflects increasing probability of cell inactivation with increasing lineal event energy. The coefficient Q is determined by the International Commission on Radiation Units and Measurements (ICRU) and based on experimental in-vitro cell survival measurements. Its analytical values are tabulated in Table 1 as a function of LET, the unrestricted linear energy transfer in water.

TABLE 1

| Quality Coefficient – Q (LET) | |
|---|---|
| LET (keV/μm) | Q (LET) |
| <10 | 1 |
| 10-100 | (0.32 × LET) – 2.2 |
| >100 | $300/(LET)^{0.5}$ |

The coefficient Q is thus a measure of the main difference between absorbed dosimetry and equivalent (radiobiological) dosimetry of radiation fields.

In addition to gas based TEPC radiation measurement devices, dosimetry systems may also utilize semiconductor detectors (e.g., solid state detectors). Solid state detectors allow for the fabrication of small sensitive volume (SV) sizes because of the availability of integrated circuit technology. SV refers to a volume that absorbs radiation energy. In some situations nanodosimetry is used instead of microdosimetry. In nanodosimetry, the small SV of the detector is used to measure absorbed dose or dose rate but with ultra-high spatial resolution. For example, metal oxide semiconductor field-effect-transistors (MOSFET) detectors (which have a very small SV of a few hundred nanometer size) are able to measure absorbed doses with submicron spatial resolution. Such detectors, however, cannot distinguish the energy deposited in the SV due to a particular event. Instead, the output signal represents the integral of many events depositing energy in the SV. This limitation also occurs with many solid state detectors, such as dosimetric diodes working in current mode, thermo-luminescent dosimeters (TLDs), and film.

Passive solid state detectors can be used to some extent in microdosimetry. For example, glow peaks in some TLDs are sensitive to the LET of particles that are associated with energy deposition on the micron level. These detectors are not a suitable substitution for TEPCs, as they do not have sensitive LET resolution and cannot be used in real time dosimetry.

A passive microdosimetry detector (e.g., '199 dosimeter) disclosed in U.S. Pat. No. 5,596,199 records the energy deposition of incident radiation using an array of microstructure non-volatile memory devices. The charge from incident charged particles is stored in an electrically insulated (floating) gate of micron or submicron scale SV of a floating gate avalanche injection metal-oxide-semiconductor (FAMOS) transistor. When this charge exceeds a threshold level, the state of the memory cell changes. The number of cells that have changed state is equal to the number of events that have deposited energy above the threshold. A predetermined initial charge is stored in each cell, which makes the charge increment required to change the state of the cells variable. This is claimed to provide a spectroscopy of the deposited energies, but it is a discreet spectroscopy rather than analogue or real spectroscopy. There can be uncertainty in the cause of the change-of-state resulting from a single event in the SV, or due to several consecutive events, thereby giving an incorrect indication of the radiation field. Owing to the passive mode of operation, the charge deposited in the SV is therefore less than on a floating gate. The charge deficit due to recombination depends on the LET of the particle. Recombination of charge in the gate oxide is well known in MOSFET detectors, and reduces the utility of MOSFET detectors for dosimetry in proton and heavy ions fields (even in an active mode). The '199 microdosimeter is designed principally to distinguish the gamma and neutron components of a radiation field, but it can only with difficultly obtain dose equivalent using the weighting coefficient Q in arbitrary radiation fields as recommended by the ICRU.

Another approach, based on the parallel connection of micron scale semiconductor detectors, such as p-n junctions, provides an active array of micron scale SVs. In this approach, reverse biased semiconductor detectors with micron scale semiconductor (e.g., silicon) SVs are connected to a nuclear spectroscopy system. The small area of the array of p-n junctions allows pile up to be avoided, provided that charge is generated in a single SV only. This condition does not hold, however, if the charged particle traverses an SV in a direction substantially parallel to the surface of the semiconductor array. In such cases energy can be deposited in two SVs simultaneously, providing a greater charge than if it was deposited in a single SV. Spectroscopy information can be converted to dose equivalent using a weighting factor recommended by the ICRU. This technique has been demonstrated using planar arrays of p-n junctions of SRAMs with an SV size of 44×44×3 microns. Applications of such planar arrays of p-n junctions for regional microdosimetry are limited owing to uncertainty in the average chord, charge collection efficiency within the SV, over-layers, and shape of the SV.

Increasing the total area of the p-n junction array leads to increases in the noise owing to an increase in capacitance that reduces the minimal LET detected by the microdosimeter. A segmentation approach with several parallel readout spectroscopy channels has been suggested to reduce the noise of the microdosimeter. This method has been demonstrated in the separation of gamma/neutron field without any qualitative or quantitative (dose equivalent) characterization of the radiation field.

Charge collection spectroscopy in a micron-size array of planar p-n junctions (e.g., SVs) of a memory chip (e.g., SRAM) strongly depends on the fabrication technology, the angle of incidence of the radiation, and the SV shape. Hence, interpretation of the measured spectra for conversion to dose equivalent values is complex. A solid state semiconductor microdosimeter based on a parallel array of p-n junctions for measurements of tissue equivalent microdosimetric spectra has also been reported. The viability of measuring integral dose and microdosimetric spectra simultaneously at the same point in a water phantom in fast neutron therapy beam has also been demonstrated.

Cells may be considered the fundamental component of life. Therefore, whole-body radiation exposure measurements may be useful in warning of generic radiation exposure, but it is the radiation absorbed by the body's cells that is the essential metric in measuring radiation damage to life forms. Traditional methods of measuring radiation safety such as using TPECs or TLDs are seriously limited because of the large scaling factor that has to be used (e.g. on the order $10^4$ or more) in order to estimate the radiation energy deposited in a cell or a cell component. This correction which scales the measured energy deposited to that which would be absorbed by an actual cell is called the Radiation Detector Correction Factor (RDCF). Reducing the RDCF helps increase the accuracy of measurements that determine the actual radiation energy absorbed by a cell.

Note that non-isotropic radiation may be poorly assessed by planar arrays of detectors because different trajectories will yield inconsistent detector signals depending on the geometry of the array to the radiation path. Thus, there is a need to build detectors that mimic the substance and dimensions of cells that will allow the closest approximation to assessing radiation deposition in cells, and make the RDCF approach the ideal value of 1.0 (no correction needed).

The energy deposited in materials is strongly dependent on the availability of conduction electrons, and different tissues absorb energy depending, in part, on their electrical characteristics. Also, for some tissues such as bone, the high relative abundance of high atomic number materials such as calcium will have a significant effect on the energy absorbed. Thus, there is a need to build detectors that can mimic the variation in electrical conductivity of different cells and thereby reduce the RDCF on a cell-type basis.

SUMMARY OF INVENTION

One feature provides a radiation dosimeter comprising a microdosimeter cell array including a first microdosimeter cell having a first semiconductor volume configured to generate a first current in response to incident radiation, the first semiconductor volume having at least one of a first size, a first shape, a first semiconductor type, and/or a first semiconductor doping type and concentration that is associated with a first biological cell type or a first biological cell component type, and a processing circuit communicatively coupled to the microdosimeter cell array and configured to generate a signal based on the first current, the signal indicative of an amount of radiation absorbed by the microdosimeter cell array. According to one aspect, the first shape includes a first surface that is planar and configured to absorb the incident radiation. According to another aspect, the first shape includes a first surface that is non-planar and configured to approximate a shape of the first biological cell type or the first biological cell component type.

According to one aspect, the first size includes a width w that is configured to approximate an average diameter of the first biological cell type or the first biological cell component type. According to another aspect, based on the first semiconductor type, the first semiconductor volume has a linear energy transfer (LET) for protons having a kinetic energy between 10 kilo-electron-volts (keV) and 100,000 keV that is configured to approximate within +/−20% a corresponding LET value of the first biological cell type or first biological cell component type. According to yet another aspect, based on the first semiconductor doping type and concentration, the first semiconductor volume has a conductivity that is configured to approximate within +/−20% a conductivity of the first biological cell type or first biological cell component type.

According to one aspect, the microdosimeter cell array further includes a second microdosimeter cell having a second semiconductor volume configured to generate a second current in response to the incident radiation, the second semiconductor volume having at least one of a second size, a second shape, a second semiconductor type, and/or a second semiconductor doping type and concentration that is associated with a second biological cell type or a second biological cell component type, and at least one of (a) the first size is different than the second size, (b) the first shape is different than the second shape, (c) the first semiconductor type is different than the second semiconductor type, and/or (d) the first semiconductor doping type and concentration is different than the second semiconductor doping type and concentration, and wherein the signal generated by the processing circuit is further based on the second current.

According to another aspect, the microdosimeter cell array further includes a third microdosimeter cell having a third semiconductor volume configured to generate a third current in response to the incident radiation, the third semiconductor volume having at least one of a third size, a third shape, a third semiconductor type, and/or a third semiconductor doping type and concentration that is associated with a third biological cell type or a third biological cell component type, and at least one of (a) the second size is different than the third size, (b) the second shape is different than the third shape, (c) the second semiconductor type is different than the third semiconductor type, and/or (d) the second semiconductor doping type and concentration is different than the third semiconductor doping type and concentration, and wherein the signal generated by the processing circuit is further based on the second current.

According to yet another aspect, the first semiconductor volume having at least one of the first size, the first shape, the first semiconductor type, and/or the first semiconductor doping type and concentration is associated with the first biological cell type, and the second semiconductor volume having at least one of the second size, the second shape, the second semiconductor type, and/or the second semiconductor doping type and concentration is associated with the second biological cell type, and the processing circuit is further configured to generate the signal based on the first current weighted by a first relative radiation sensitivity scaling factor and the second current weighted by a second relative radiation sensitivity scaling factor, the first relative radiation sensitivity scaling factor based on radiation sensitivity of the first biological cell type relative to at least radiation sensitivity of the second biological cell type, and the second relative radiation sensitivity scaling factor based on radiation sensitivity of the second biological cell type relative to at least radiation sensitivity of the first biological cell type.

According to another aspect, the first semiconductor volume having at least one of the first size, the first shape, the first semiconductor type, and/or the first semiconductor doping type and concentration is associated with the first biological cell component type, and the second semiconductor volume having at least one of the second size, the second shape, the second semiconductor type, and/or the second semiconductor doping type and concentration is associated with the second biological cell component type, and the processing circuit is further configured to generate the signal based on the first current weighted by a first relative radiation sensitivity scaling factor and the second current weighted by a second relative radiation sensitivity scaling factor, the first relative radiation sensitivity scaling factor based on radiation sensitivity of the first biological cell component type relative to at least radiation sensitivity of the second biological cell component type, and the second relative radiation sensitivity scaling factor based on radiation sensitivity of the second biological cell component type relative to at least radiation sensitivity of the first biological cell component type.

Another feature provides a method comprising providing a first microdosimeter cell having a first semiconductor volume configured to generate a first current in response to incident radiation, forming the first semiconductor volume such that the first semiconductor volume has at least one of a first size, a first shape, a first semiconductor type, and/or a first semiconductor doping type and concentration that is associated with a first biological cell type or a first biological cell component type, and coupling a processing circuit to the first microdosimeter cell, the processing circuit configured to generate a signal based on the first current, the signal indicative of an amount of radiation absorbed by the first microdosimeter cell. According to one aspect, the method further comprises forming the first semiconductor volume such that the first size includes a width w that is substantially equal to an average diameter of the first biological cell type or the first biological cell component type. According to another aspect, the method further comprises forming the first semiconductor volume such that the first semiconductor type has a linear energy transfer (LET) for protons having a kinetic energy between 10 kilo-electron-volts (keV) and 100,000 keV that is within +/−20% of a corresponding LET value of the first biological cell type or first biological cell component type. According to yet another aspect, the method further comprises forming the first semiconductor volume such that the first semiconductor doping type and concentration has a conductivity that is within +/−20% a conductivity of the first biological cell type or first biological cell component type.

According to one aspect, the method further comprises providing a second microdosimeter cell having a second semiconductor volume configured to generate a second current in response to the incident radiation, forming the second semiconductor volume such that the second semiconductor volume has at least one of a second size, a second shape, a second semiconductor type, and/or a second semiconductor doping type and concentration that is associated with a second biological cell type or a second biological cell component type, and at least one of (a) the first size is different than the second size, (b) the first shape is different than the second shape, (c) the first semiconductor type is different than the second semiconductor type, and/or (d) the first semiconductor doping type and concentration is different than the second semiconductor doping type and concentration, and coupling the second microdosimeter cell to the processing circuit, the processing circuit further configured to generate the signal also based on the second current, the signal indicative of an amount of radiation absorbed by the first and second microdosimeter cells.

According to another aspect, the first semiconductor volume formed has at least one of the first size, the first shape, the first semiconductor type, and/or the first semiconductor doping type and concentration associated with the first biological cell type, and the second semiconductor volume formed has at least one of the second size, the second shape, the second semiconductor type, and/or the second semiconductor doping type and concentration associated with the second biological cell type, and the processing circuit is further configured to generate the signal based on the first current weighted by a first relative radiation sensitivity scaling factor and the second current weighted by a second relative radiation sensitivity scaling factor, the first relative radiation sensitivity scaling factor based on radiation sensitivity of the first biological cell type relative to at least radiation sensitivity of the second biological cell type, and the second relative radiation sensitivity scaling factor based on radiation sensitivity of the second biological cell type relative to at least radiation sensitivity of the first biological cell type.

Another feature provides a radiation dosimeter that approximates radiation absorbed by biological matter. The radiation dosimeter comprises a first microdosimeter cell including a first semiconductor volume, a first cell first semiconductor region, and a first cell second semiconductor region, the first semiconductor volume configured to generate a first current in response to radiation incident upon the radiation dosimeter, the first current configured to flow between the first cell first semiconductor region and the first cell second semiconductor region, and wherein the first microdosimeter cell includes a first size, a first semiconductor type, and/or a first semiconductor doping type and concentration that is based on a first biological cell type or a first biological cell organelle type, a processing circuit communicatively coupled to the first microdosimeter cell and configured to generate a signal based on the first current, the signal indicative an amount of the radiation absorbed the radiation dosimeter, and a display communicatively coupled to the processing circuit and configured to display a radiation level reading based on the signal generated.

According to one aspect, based on the first semiconductor type, the first semiconductor volume has a linear energy transfer (LET) for protons having a kinetic energy between 10 kilo-electron-volts (keV) and 100,000 keV that is within +/−20% a corresponding LET value of the first biological cell type or first biological cell organelle type. According to another aspect, the radiation dosimeter further comprises a second microdosimeter cell including a second semiconductor volume, a second cell first semiconductor region, and a second cell second semiconductor region, the second semiconductor volume configured to generate a second current in response to the radiation incident upon the radiation dosimeter, the second current configured to flow between the second cell first semiconductor region and the second cell second semiconductor region, and wherein the second microdosimeter cell includes a second size, a second semiconductor type, and/or a second semiconductor doping type and concentration that is based on a second biological cell type or a second biological cell organelle type, and at least one of (a) the first size is different than the second size, (b) the first semiconductor type is different than the second semiconductor type, and/or (c) the first semiconductor doping type and concentration is different than the second semiconductor doping type and concentration, and wherein the signal generated by the processing circuit is further based on the second current.

According to yet another aspect, the first microdosimeter cell including at least one of the first size, the first semiconductor type, and/or the first semiconductor doping type and concentration is based on the first biological cell type, and the second microdosimeter cell including at least one of the second size, the second semiconductor type, and/or the second semiconductor doping type and concentration is based on the second biological cell type, and the processing circuit is further configured to generate the signal based on the first current weighted by a first relative radiation sensitivity scaling factor and the second current weighted by a second relative radiation sensitivity scaling factor, the first relative radiation sensitivity scaling factor based on radiation sensitivity of the first biological cell type relative to at least radiation sensitivity of the second biological cell type, and the second relative radiation sensitivity scaling factor based on radiation sensitivity of the second biological cell type relative to at least radiation sensitivity of the first biological cell type.

BRIEF DESCRIPTION OF THE DRAWINGS

FIG. 18 illustrates a table that shows exemplary relative radiation sensitivity scaling factors for various biological cell types associated with a biological organism.

FIG. 19 illustrates another table that shows exemplary relative radiation sensitivity scaling factors for various biological cell component/organelle types associated with a biological cell.

DETAILED DESCRIPTION

Figure 1:
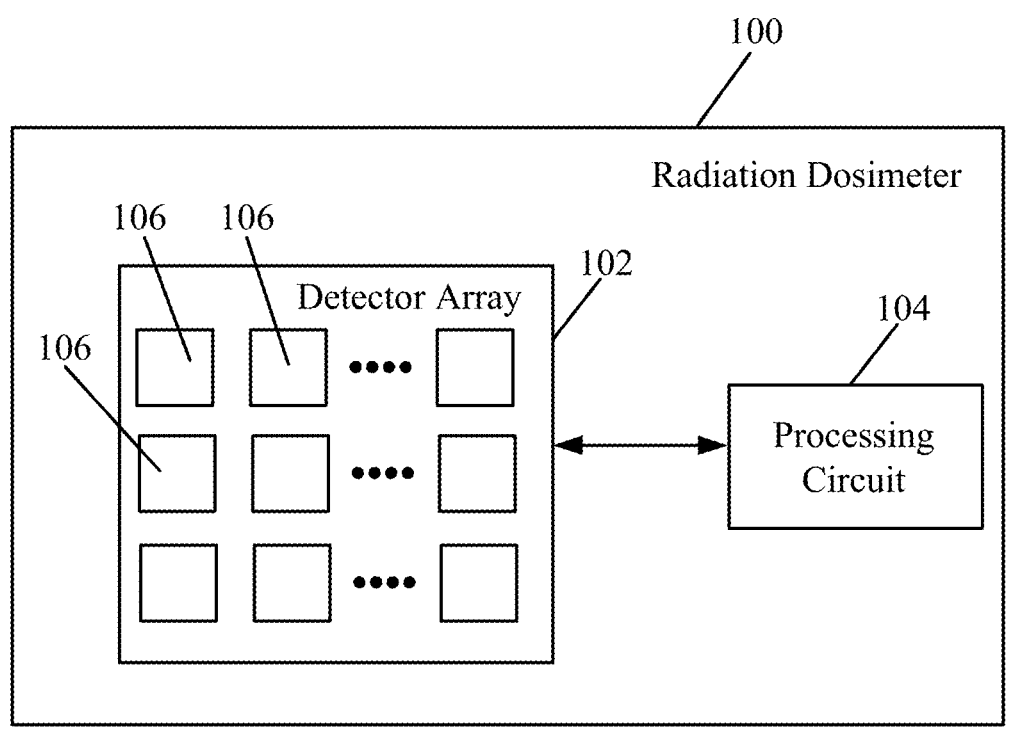
FIG. 1 illustrates a schematic block diagram of a radiation microdosimeter.

In the following description, specific details are given to provide a thorough understanding of the various aspects of the disclosure. However, it will be understood by one of ordinary skill in the art that the aspects may be practiced without these specific details. For example, circuits may be shown in block diagrams in order to avoid obscuring the aspects in unnecessary detail. In other instances, well-known circuits, structures and techniques may not be shown in detail in order not to obscure the aspects of the disclosure.

The word "exemplary" is used herein to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage or mode of operation. The term "communicatively coupled" is used herein to mean that two or more elements may communicate with one another (e.g., by transmitting signals between them) either directly or indirectly and via wirelessly or through wired connection.

The terms wafer and substrate may be used herein to include any structure having an exposed surface with which to form an integrated circuit (IC) according to aspects of the present disclosure. The term substrate is understood to include semiconductor wafers. The term substrate is also used to refer to semiconductor structures during fabrication, and may include other layers that have been fabricated thereupon. The term substrate includes doped and undoped semiconductors, epitaxial semiconductor layers supported by a base semiconductor, or semiconductor layers supported by an insulator, as well as other semiconductor structures well known to one skilled in the art. The term insulator is defined to include any material that is less electrically conductive than materials generally referred to as conductors by those skilled in the art. The term "horizontal" is defined as a plane substantially parallel to the conventional plane or surface of a wafer or substrate, regardless of the orientation of the wafer or substrate. The term "vertical" refers to a direction substantially perpendicular to the horizontal as defined above. Prepositions, such as "on," "upper," "side," "higher," "lower," "over," and "under" when used with respect to the integrated circuits described herein are defined with respect to the conventional plane or surface being on the top surface of the wafer or substrate, regardless of the orientation of the wafer or substrate. The prepositions "on," "upper," "side," "higher," "lower," "over," and "under" are thereby defined with respect to "horizontal" and "vertical."

P-type conductivity is conductivity associated with holes in a semiconductor material, and n-type conductivity is conductivity associated with electrons in a semiconductor material.

Overview

A radiation detector that has the shape and/or size of an individual biological cell type or cell component type is disclosed. The radiation detector may also be fabricated to approximate the biological cell or cell component type's absorption of radiation. For example, this may be accomplished by fabricating the detector with different semiconductors, and/or using various dopants to adjust for approximate cell composition and absorption characteristics. It is noted that human tissue cells vary with tissue function. In general, radiation is most deleterious to cells whose function involves continuous cell division, such as, but not limited to spermatogonia, erythroblasts, epidermal stem cells, and gastrointestinal stem cells. Other cells that do not necessarily involve rapid, continuous cell division yet are still very sensitive to radiation are oocytes and lymphocytes. Thus, the radiation detector may include an array of semiconductor detectors each having different sizes, shapes, and dopants— to mimic the cells found in biological tissue that is, for example, especially sensitive to radiation, such as the aforementioned cell types. The different detectors of the array can have individual "quality factors" (the RDCF for specific cell types), and the total radiation exposure level can be determined by weighting the various detectors by their distribution in the body.

Since the detector arrays may be very small, they may be shielded by tissue-equivalent absorbers to mimic the radiation reaching them if they are deep within the body. Such tissue-equivalent absorbers may be plastics such as polyethylene or water. In some aspects, this may help increase the accuracy of measuring absorbed radiation.

According to one aspect, the present disclosure provides a microdosimeter, comprising an array of three-dimensional p-n junction semiconductor detectors, each providing a sensitive volume-target (e.g., semiconductor volume) that correlates to cells or cell components. The semiconductor volume may be further encased or covered by a tissue equivalent medium to better approximate the radiation reaching the cell or cell component that the microdosimeter cell array mimics. The tissue equivalent medium generates secondary charged particles that may also be detected and measured by the semiconductor volume.

According to one aspect, the radiation detector may approximate the size of specific cells in tissue, such as, but not limited to, white blood cells, bone cells, gastro-intestinal cells. According to another aspect, the radiation detector may approximate the size of cell components, such as, but not limited to, a cell nucleolus. According to another aspect, the detector may approximate the radiation absorption characteristics of specific cells and/or cell components by doping the semiconductor of the detector to equivalent electrical characteristics. According to yet another aspect, the detector may approximate the radiation absorption characteristics of specific cells and/or cell components by doping the semiconductor to equivalent radiation absorption characteristics. According to another aspect, the detector may approximate the radiation absorption characteristics of specific cells and/or cell components by using a semiconductor that has equivalent radiation absorption characteristics.

Biological cells from different tissues of the body differ from one another across a wide range of features and characteristics including but not limited to their size, shape, electrical conductivity, and linear energy transfer (LET) values (i.e., the linear density of energy lost by ionizing particles travelling through cell). Similarly, different biological cell components within a single cell also differ from one another across, among other things, their size, shape, electrical conductivity, and LET values. Notably, the microdosimeters described herein feature detector cells that include semiconductor volumes that have at least one of a size, shape, electrical conductivity, and/or LET value(s) that correspond to and approximately match the size, shape, electrical conductivity, and/or LET value(s) of a biological cell type or biological cell component type in order to reduce the Radiation Detector Correction Factor (RDCF) needed and thus better approximate the actual radiation absorbed by the biological cell type or cell component type.

Exemplary Microdosimeter

FIG. 1 illustrates a schematic block diagram of a radiation microdosimeter 100 according to one aspect of the present disclosure. The microdosimeter 100 includes a detector array 102 coupled to a processing circuit 104. The detector array 102 includes one or more individual detectors 106 (may also be referred to herein as "detector cells" and "microdosimeter cells"). As will be explained in greater detail below, the detectors 106 generate a current in proportion to the amount of ionizing radiation they are exposed to. The processing circuit 104 receives and/or monitors the current generated by the detectors 106 and then calculates a radiation level value based on the current. The microdosimeter 100 may then display the radiation level value calculated to a user of the microdosimeter 100 in order to ascertain potential bodily harm from radiation exposure. According to one example, the processing circuit 104 is configured to generate a signal based on the one or more currents generated by the one or more detectors 106, and the signal generated is indicative of an amount of radiation absorbed by the microdosimeter cell array 102.

Figure 2:
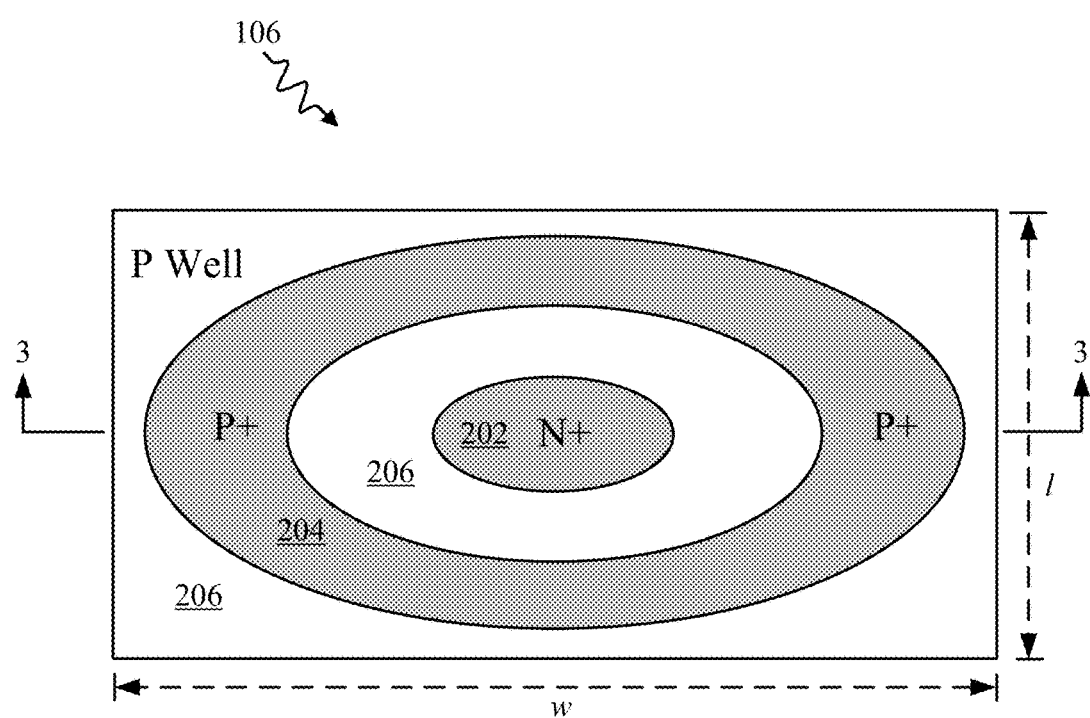
FIG. 2 illustrates a schematic top view of a detector cell of the radiation microdosimeter.
Figure 3:
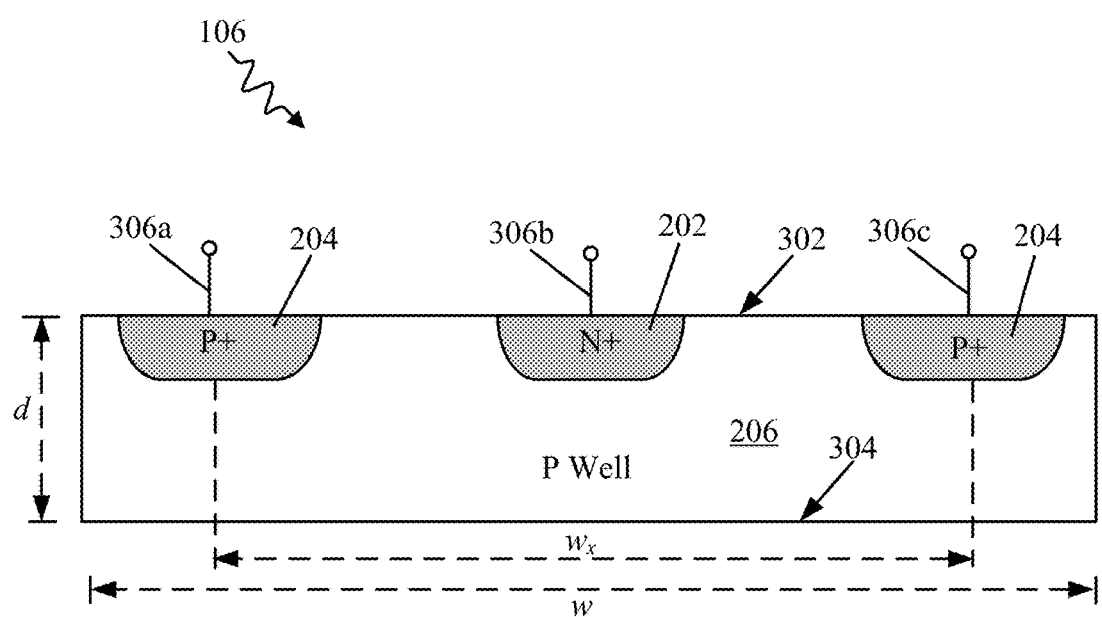
FIG. 3 illustrates a schematic cross-sectional view of the detector cell.

FIGS. 2 and 3 illustrate schematic views of a single detector cell 106 according to one aspect. Specifically, FIG. 2 shows a top view of the detector 106, and FIG. 3 shows a cross-sectional view of the detector 106 taken along the line 3-3 of FIG. 2. Referring to FIGS. 2 and 3, the radiation microdosimeter cell 106 comprises a first semiconductor region 202 and a second semiconductor region 204. The first semiconductor region 202 may be a heavily doped n-type semiconductor region (e.g., N+ region) and the second semiconductor region 204 may be a heavily doped p-type semiconductor region (e.g., P+ region). In this example, the second semiconductor region 204 forms a concentric oval-shaped ring that surrounds the inner, first semiconductor region 202. The first and second semiconductor regions 202, 204 may reside in a p-type semiconductor well 206. The p-type semiconductor well 206 may contain concentrations of a p-type dopant (e.g., boron, gallium, etc.) that are order(s) of magnitude less than the heavily doped p+-type semiconductor region 204. Both the first and second semiconductor regions 202, 204 serve as contact points for electrical conductors 306a, 306b, 306c, such as ohmic contacts. The electrical conductors 306a, 306b, 306c transmit current signals generated within the detector 106 to the processing circuit 104 (see FIG. 1). Although in the example illustrated in FIGS. 2-3 the first semiconductor region 202 includes one electrical contact 306b, according to other examples the first semiconductor region 202 may have a plurality of contacts. Similarly, in the example shown the second semiconductor region 204 includes two electrical contacts 306a, 306c, but in other aspects it may include any number of electrical contacts equal to or greater than one (1).

Each detector cell of the microdosimeters described herein has a "radiation-sensitive semiconductor volume" associated with it that—as will be more fully described below—absorbs ionizing radiation, and in response generates currents (e.g., an electron current and a hole current created by electron-hole pairs) proportional to the amount of radiation absorbed. Thus, the radiation-sensitive semiconductor volume (also referred to herein as "semiconductor volume") comprises that portion of the detector cell's semiconductor material that is capable of absorbing the ionizing radiation and generating the aforementioned currents.

For example, referring to FIGS. 2 and 3, the semiconductor volume includes at least the semiconductor well 206. Thus, according to one aspect, the detector's 106 semiconductor volume (SV) may be equal to the detector width w multiplied by the detector length l multiplied by the detector depth d less the volumes $V_{R1}$ and $V_{R2}$ occupied by the first and second semiconductor regions 202, 204, respectively (equation (1)).

$$SV = w*l*d - (V_{R1} + V_{R2}) \quad (1).$$

According to another aspect, in addition to the semiconductor well 206, the semiconductor volume may further include the first and/or second semiconductor regions 202, 204. Thus, according to one aspect, the detector's 106 semiconductor volume may be equal to the detector width w multiplied by the detector length l multiplied by the detector depth d (equation (2)).

$$SV = w*l*d \quad (2).$$

The microdosimeter cell 106 may also have a device width w, that extends from the midpoint of one end of the second semiconductor region 204 to the midpoint of another end (directly across the diameter) of the second semiconductor region 204 as shown in FIG. 3.

Figure 4:
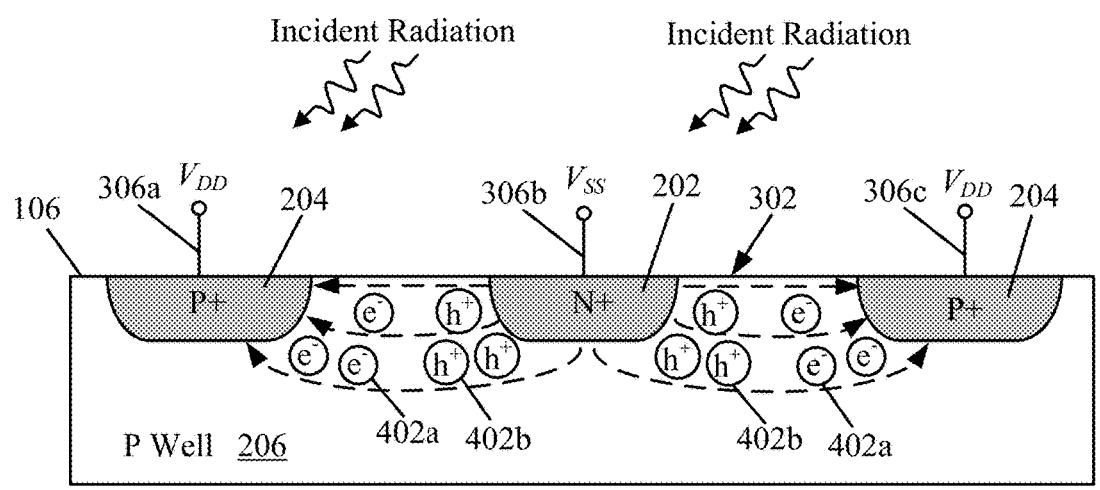
FIG. 4 illustrates another schematic cross-sectional view of the detector cell.

FIG. 4 also illustrates a schematic cross-sectional view of the detector 106 taken along the line 3-3 of FIG. 2. Specifically, FIG. 4 demonstrates the effects of ionizing incident radiation upon a first surface 302 (e.g., top surface) of the detector 106 according to one aspect of the disclosure. The ionizing incident radiation may be, for example, cosmic rays, alpha particles, beta particles, gamma rays, x-rays, neutrons, and/or generally any charged particle moving at relativistic speeds. In the illustrated example, the detector's semiconductor volume (e.g., p-type well 206) absorbs at least a portion of the incident radiation energy. As the semiconductor volume absorbs radiation energy, electron-hole pairs 402a, 402b are generated in the semiconductor volume as shown. The greater the amount of radiation energy absorbed by the semiconductor volume the greater the number of electron-hole pairs 402a, 402b generated. When a voltage is applied between the first and second semiconductor regions 202, 204 as shown (e.g., positive supply voltage $V_{DD}$ applied to the P+ type second semiconductor region 204 and ground $V_{SS}$ applied to N+ type first semiconductor region 202), an electric field (indicated by the dashed arrows) is created within the semiconductor volume.

The electron-hole pairs 402a, 402b generated by the absorbed radiation are drawn apart by the electrical field such that electrons 402a move to the P+ type semiconductor region 204 electrical contacts 306a, 306c and holes 402b move to the N+ type semiconductor region 202 electrical contact 306b. These charges 402a, 402b produce a current within the semiconductor volume that can be measured and analyzed to determine the amount of radiation absorbed in the semiconductor volume. According to one example, the electron 402a current flowing toward the P+ type semiconductor region electrical contacts 306a, 306c may be analyzed rather than the hole 402b current flowing to the N+ type semiconductor region electrical contact 306b since the electrons 402a generated by the absorbed radiation have approximately three times the velocity (mobility) of the holes 402b. For example, the electron 402a current flowing into the P+ type semiconductor region 204 may form a sharper electronic pulse than the hole current flowing into the N+ type semiconductor region 202. In other examples, both the electron 402a current and/or the 402b hole current may be analyzed to determine the radiation absorbed.

As will be described in more detail below, the semiconductor volume of the detector 106 is designed/manufactured to mimic a specific biological cell or biological cell component. Biological cells from various tissues of the body differ from one another across a wide range of features and characteristics including, but not limited to, their size, shape, electrical conductivity, and LET values. Similarly, different biological cell components within a single cell also differ from one another across, among other things, their own size, shape, electrical conductivity, and LET values. Notably, the microdosimeters described herein feature detector cells that include semiconductor volumes that have at least one of a size, shape, electrical conductivity, and/or LET value(s) that approximately match the size, shape, electrical conductivity, and/or LET value(s) of a biological cell or biological cell component in order to reduce the RDCF needed and thus better approximate the actual radiation absorbed by the biological cell or cell component.

Figure 5:
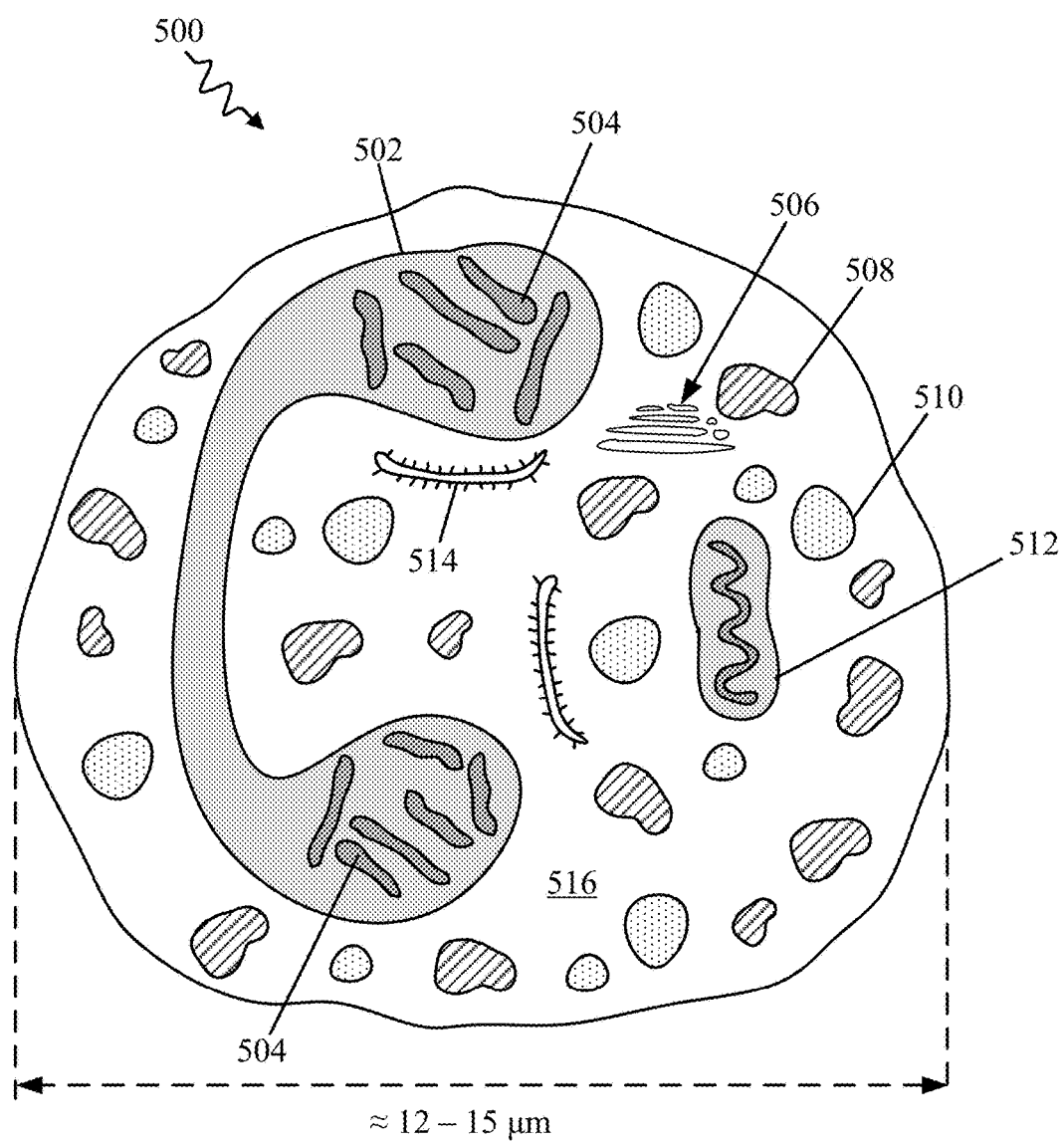
FIG. 5 illustrates a schematic cross-sectional view of a human neutrophil white blood cell.

FIG. 5 illustrates a schematic, cross-sectional view of a human neutrophil white blood cell 500 according to one aspect. The white blood cell 500 is just one example of a biological cell that the detector 106 may be designed to mimic (e.g, size, shape, electrical conductivity, and/or LET value) in order to approximate the radiation absorbed by the biological cell. White blood cells are one of the body's cells that are most sensitive to radiation exposure, and neutrophils 500 account for about 50% to 70% of the total white blood cells in the human body. Among other organelles, a neutrophil white blood cell includes a nucleus 502 having genetic material 504, golgi apparatus 506, specific granules 508, azurophil granules 510, mitochondrion 512, and endoplasmic reticulum 514, all of which are suspended within the neutrophil's cytoplasm 516. A typical neutrophil cell 500 is generally spherical and is about 12-15 µm in diameter. The neutrophil's components 502, 504, 506, 508, 510, 512, 514 may have various shapes and sizes, and are smaller than the neutrophil cell 500 itself. For example, the specific granules 508 and azurophil granules 510 may be generally spherical and have a diameter of about 1 µm. Mitochondrion typically have a length that is about 0.5 µm to 1.0 µm.

The electrical conductivity of the neutrophil cell 500 may vary depending the state of the immune system of the host (e.g., whether the immune system is responding to an infection, toxin, etc.). Given a specific state of the immune system, the electrical conductivity of the neutrophil cell 500 and/or neutrophil cell's components 502, 504, 506, 508, 510, 512, 514 may be empirically collected and tabulated. Similarly, the LET values of the neutrophil cell 500 and/or its individual cell components 502, 504, 506, 508, 510, 512, 514 that are associated with various charged particles (e.g., alpha particles, protons, neutrons, beta particles, etc.) may also be empirically collected and tabulated.

According to one example, a detector 106 or a plurality of detectors 106 within a microdosimeter 100 may be designed/manufactured to mimic a neutrophil cell 500 and/or any one of the neutrophil cell components 502, 504, 506, 508, 510, 512, 514. Specifically, at least one of the plurality of detectors 106 of the microdosimeter 100 may be fabricated so that at least one of its size, shape, electrical conductivity, and/or LET value(s) approximates that of a neutrophil cell 500 or component 502, 504, 506, 508, 510, 512, 514.

For example, the width w, length l, and depth d of the detector's semiconductor volume (e.g., well 206) may be sized so as to approximate the average dimensions and/or average volume of the neutrophil cell 500 (e.g., resulting in a substantially cube-shaped structure 12-15 µm across). As another example, the width w, length l, and depth d of the detector's semiconductor volume may be sized so as to approximate the average dimensions and/or average volume of any one of the neutrophil cell's components 502, 504, 506, 508, 510, 512, 514. Of course, the width w, length l, and depth d of the detector's semiconductor volume may be sized so as to approximate the average dimensions and/or average volume of any biological cell type or biological cell component type.

Figure 6:
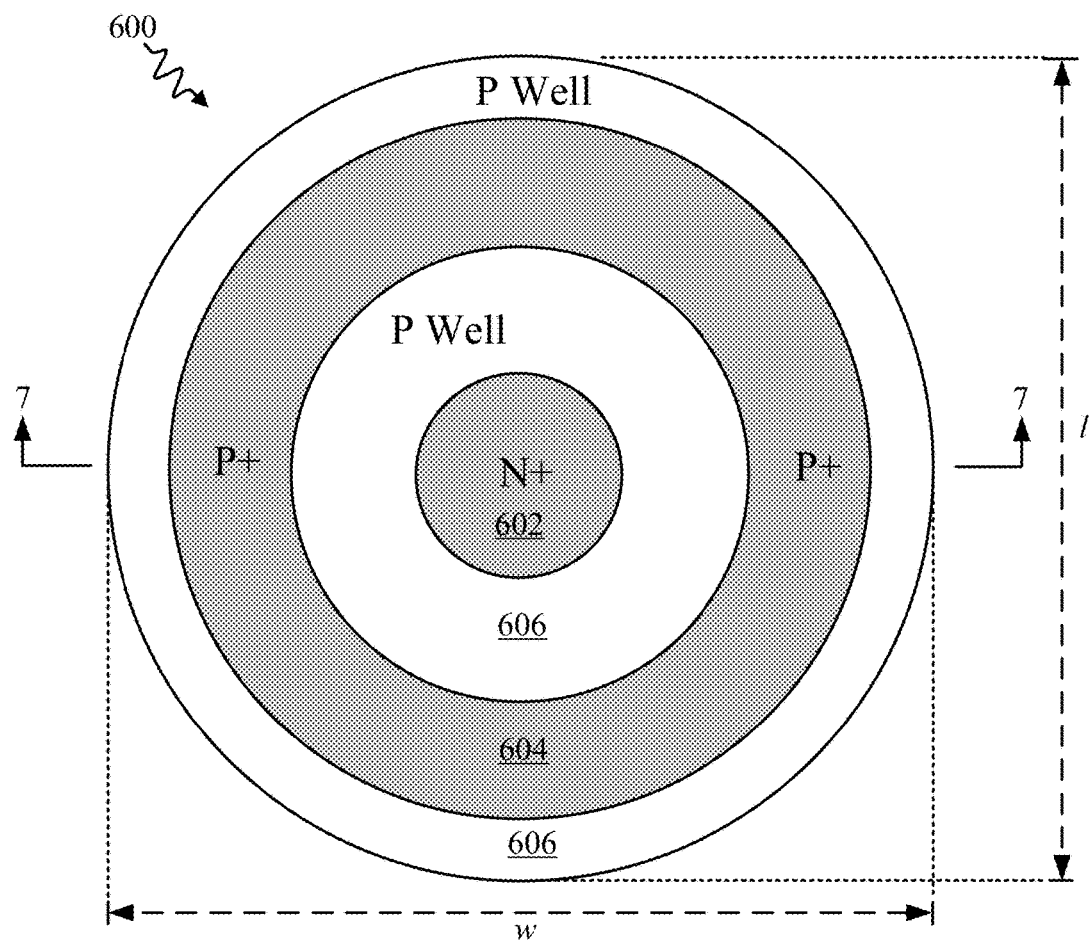
FIG. 6 illustrates a schematic top view of a detector cell having a semi-circular shape.
Figure 7:
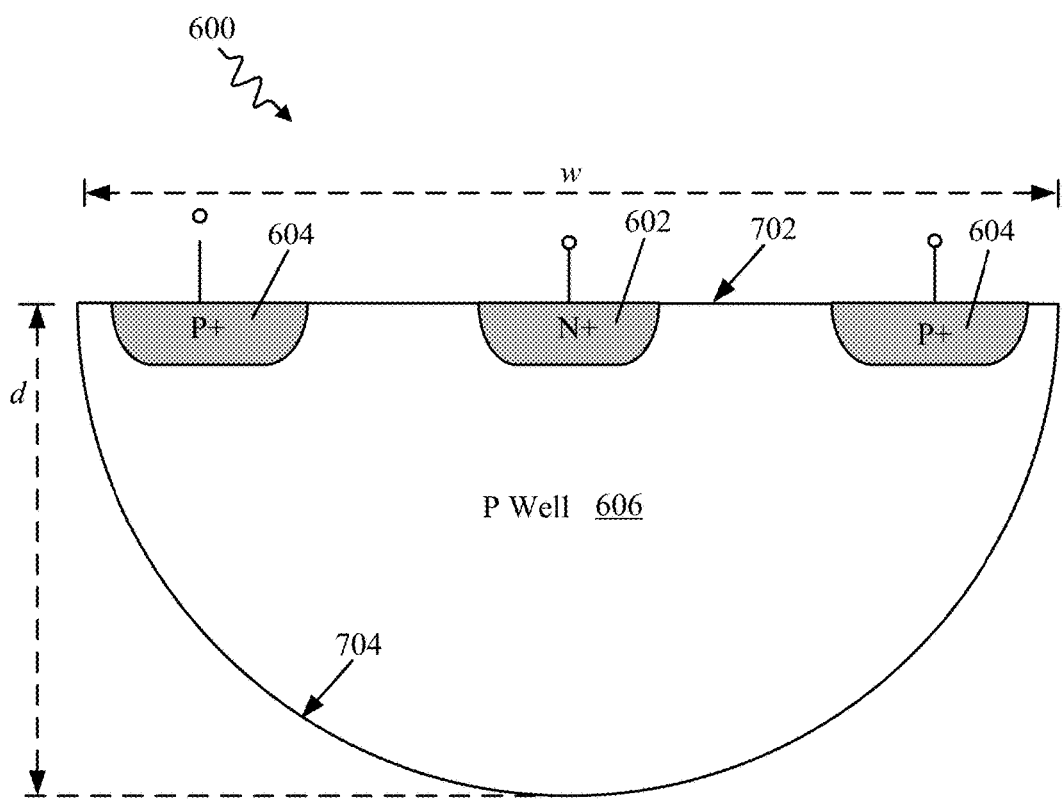
FIG. 7 illustrates a schematic cross-sectional view of the detector cell having the semi-circular shape.

Moreover, the detector's semiconductor volume (e.g., well 206) may be fabricated such that its shape, at least in part, approximates the shape of the neutrophil cell 500. For example, FIGS. 6 and 7 illustrate a detector 600 substantively similar in operation to the detector 106 of FIG. 1. For example, the detector 600 still comprises a heavily doped n-type first semiconductor region 602 and a heavily doped p-type second semiconductor region 604 formed within a p-type well 606. However, the semiconductor volume (e.g., the p-type well 606) of the detector 600 shown in FIGS. 6 and 7 has a semi-spherical shape (e.g., width w and length l are approximately equal and the depth d is w/2). That is, the semiconductor volume bounded by the planar, first surface (e.g., top surface) 702 and the curved, second surface 704 forms a semi-spherical shape. In this fashion, the detector 600 may approximate the shape of half of the neutrophil cell 500 or half of the neutrophil's components that also have spherical shapes (e.g., granules 508, 510). The other half of the neutrophil cell 500 or neutrophil component 508, 510 may be approximated with another semi-spherical shaped detector within the microdosimeter 100, which may have a plurality/array of detectors 106, 600. Generally, the detector's semiconductor volume may be fabricated such that its shape, at least in part, approximates the shape of any of the neutrophil's components 502, 504, 506, 508, 510, 512, 514.

Furthermore, the detector's semiconductor volume may be fabricated with a semiconductor material having a particular doping concentration that approximates the conductivity of the neutrophil cell 500 or cell component 502, 504, 506, 508, 510, 512, 514. For example, the semiconductor volume may be doped with various elements (e.g., phosphorus if the semiconductor volume is n-type, or boron if the semiconductor volume is p-type) to various degrees in order to replicate the conductivity of the neutrophil cell 500 or component 502, 504, 506, 508, 510, 512, 514. Silicon may be doped to change its conductivity by over six orders of magnitude. For example, single-crystal silicon doped with phosphorus to a level of $10^{12}/cm^3$ may have a resistivity of approximately 25,000 Ω-cm, which can be used to mimic the resistivity of cells or cell components that are as conductive as insulators (e.g., cortical bone cells). By contrast, doping the single-crystal silicon to $10^{19}/cm^3$ may provide a resistivity of about 0.01 Ω-cm, which may be used to mimic cell components that are as conductive as common conductors (e.g., cell or cell components that are predominantly saline). Since most if not all cells, cell components (e.g., organelles), and tissues lie within this range of conductivity, the detector's 106 semiconductor volume (e.g., p-type well 206) may be doped with, for example, boron to a doping concentration between the above given range. According to one aspect, the semiconductor volume's semiconductor doping type and concentration may be adjusted such that the first semiconductor volume has a conductivity that is configured to approximate within +/−5%, +/−10%, +/−15%, +/−20%, +/−25%, +/−30%, +/−35%, +/−40%, +/−45%, or +/−50% of the conductivity of the first biological cell type or first biological cell component type that the microdosimeter cell's semiconductor volume is attempting to mimic.

For instance, in order to mimic the conductivity of a neutrophil cell 500, which contains a moderate amount of ions and water, the boron doping concentration may be closer to higher end of the range (i.e., closer to the $10^{19}/cm^3$). The conductivity of the neutrophil components 502, 504, 506, 508, 510, 512, 514 may be similarly mimicked by varying the doping concentration of boron within the p-type well 206 of other detector 106 cells until the p-type well 206 conductivity matches the conductivity of a given cell component 502, 504, 506, 508, 510, 512, 514.

Additionally, the detector's semiconductor volume may be fabricated using a semiconductor material and/or combination of materials that approximate the LET values (for one or more ionizing radiation particles) of the neutrophil cell 500 or cell component 502, 504, 506, 508, 510, 512, 514. As discussed in greater detail below, some semiconductors, such as silicon and germanium, have LET value characteristics that closely match the LET value characteristics of different types of body tissues/cells. Therefore, germanium, silicon, and/or even carbon may be used to fabricate the semiconductor volume (e.g., p-type well 206) of the detector 106 until its LET values closely match the LET values of the neutrophil cell 500 or cell component 502, 504, 506, 508, 510, 512, 514.

As discussed above, the detector cell's 106 semiconductor volume may be sized, shaped, and fabricated (e.g., doping concentration and semiconductors used) to match the neutrophil cell 500 as a whole. Alternatively, the microdosimeter 100 comprising an array of detectors 106 (see FIG. 1) may have at least one detector that is sized, shaped, and fabricated to approximate each neutrophil component/organelle (e.g., golgi apparatus, mitochondrion, etc.) 502, 504, 506, 508, 510, 512, 514. For example, one or more detectors 106 may be sized, shaped, and fabricated to match the size, shape, electrical conductivity, and/or LET values of the nucleus 502, while another one or more detectors 106 may be sized, shaped, and fabricated to match the size, shape, electrical conductivity, and/or LET values of the mitochondrion 512, and so on. In this fashion, the radiation exposure for the entire neutrophil cell 500 may be determined piecemeal by determining the radiation exposure to each cell component 502, 504, 506, 508, 510, 512, 514. According to one aspect, the determined radiation exposure for each cell component 502, 504, 506, 508, 510, 512, 514 may be weighted with a sensitivity factor (e.g., indicative of the sensitivity to radiation and the importance of that component) and summed together to determine the final radiation exposure of the entire cell. Since the detector's 106 semiconductor volume may be fabricated smaller than 0.1 μm in diameter (e.g., width w and/or length l in FIG. 2), the radiation exposure of even the smallest cellular components of the neutrophil cell 500 may be approximated.

The discussion above related to designing/manufacturing the detector 106 to approximate the characteristics of a neutrophil cell 500 or its components 502, 504, 506, 508, 510, 512, 514 are merely examples. In practice any of the detectors described herein may be designed/manufactured so that their size, shape, electrical conductivity, LET values, and/or other characteristics that affect radiation absorption approximate the corresponding feature of a biological tissue, cell, or cell component (e.g., organelle). Such biological tissues, cells, and cell components are not limited to human tissues, cells, and cell components.

Figure 8:
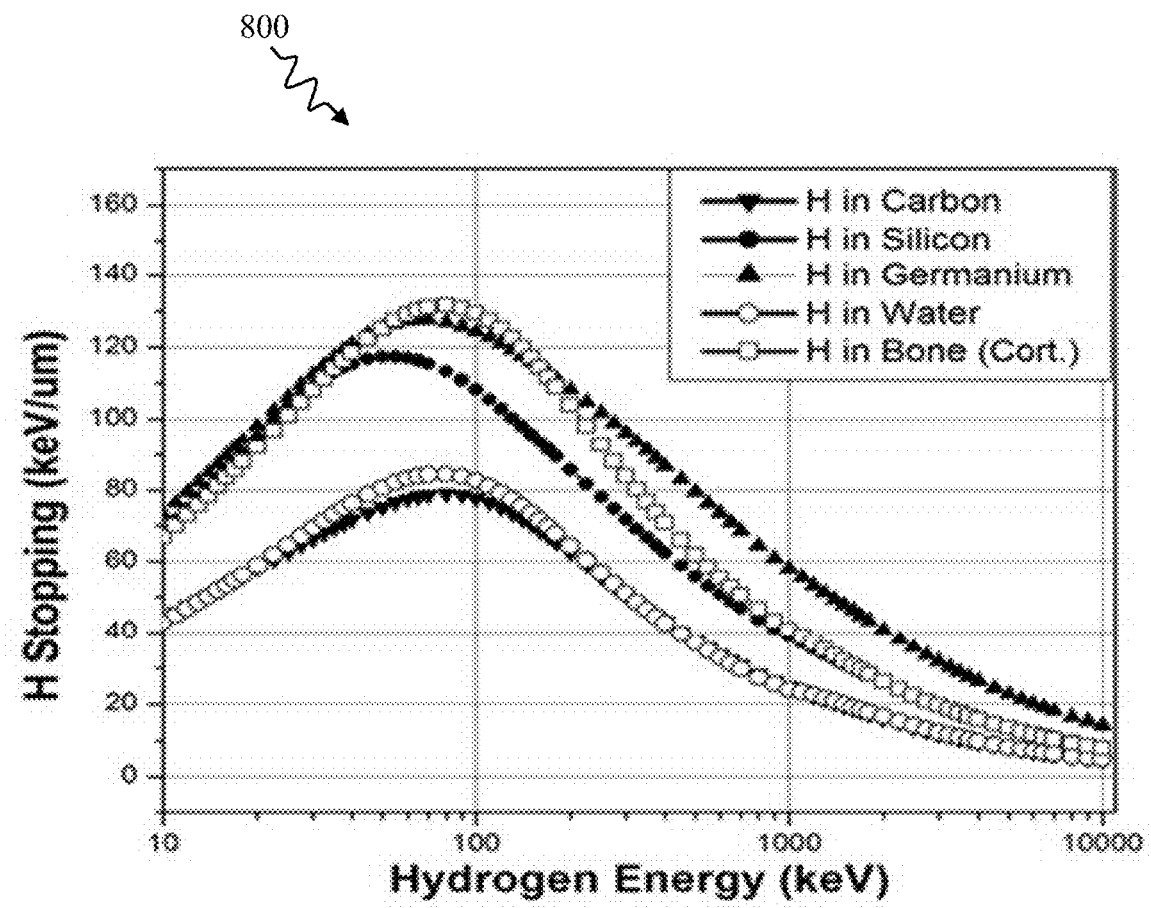
FIG. 8 illustrates an exemplary LET plot that shows the energy loss of a proton/hydrogen nuclei traveling through three types of semiconductors, water, and cortical bone.

FIG. 8 illustrates an exemplary LET plot 800 that shows the energy loss of a proton/hydrogen nuclei (e.g., one type of ionizing radiation) traveling through three types of semiconductors (e.g., carbon, silicon, and germanium), water, and cortical bone. On the vertical axis, the energy loss is measured in kilo-electron-volt per micrometer (keV/μm), which translates to about 300 electron/hole pairs created within a given medium per μm of path length. As shown in the plot 800, germanium absorbs a greater amount of radiation energy from a proton traveling through it per μm than silicon, which in turn absorbs a greater amount of radiation energy from a proton traveling through it per μm than carbon. Notably, it may be observed that germanium and cortical bone have very similar LET value characteristics compared to one another when the kinetic energy of the proton is less than about 300 keV. For example, for a proton having a kinetic energy of 100 keV, germanium and cortical bone have LET values that are within about 5% of each other. For a proton having a kinetic energy of 300 keV, germanium and cortical bone have LET values that are within about 15% of each other. Similarly, silicon and cortical bone have very similar LET value characteristics compared to one another when the kinetic energy of the proton is greater than about 300 keV. For example, for a proton having a kinetic energy of 1000 keV, silicon and cortical bone have LET values that are within 5% of each other. According to the plot 800 shown, carbon and water have very similar LET value characteristics as well. For example, for a proton having a kinetic energy between 100 and 100,000 keV, carbon and water have LET values that are within 8% of each other or less. Most biological tissues, cells, and cell components have LET value characteristics that lie in between these curves.

Consequently, germanium and/or silicon may be used to fabricate a detector's semiconductor volume (e.g., well, such as p-type well 206) in cases where the detector is attempting to replicate the radiation absorption characteristics of bone tissue/cells, since bone tissue has a relatively high LET value compared to other tissues/cells. Similarly, carbon may be used, at least in part, to fabricate a detector's semiconductor volume (e.g., well, such as p-type well 206) in cases where the detector is attempting to replicate the radiation absorption characteristics of a tissue, cell, or cell component that has a relatively low LET value compared to other tissues/cells. A detector's semiconductor volume may be fabricated using a combination of germanium, silicon, and/or carbon according to varying proportions to one another to replicate the LET value characteristics of various tissues, cells, or cell components that have LET values that lie between the LET values of carbon, silicon, and germanium.

Figure 9:
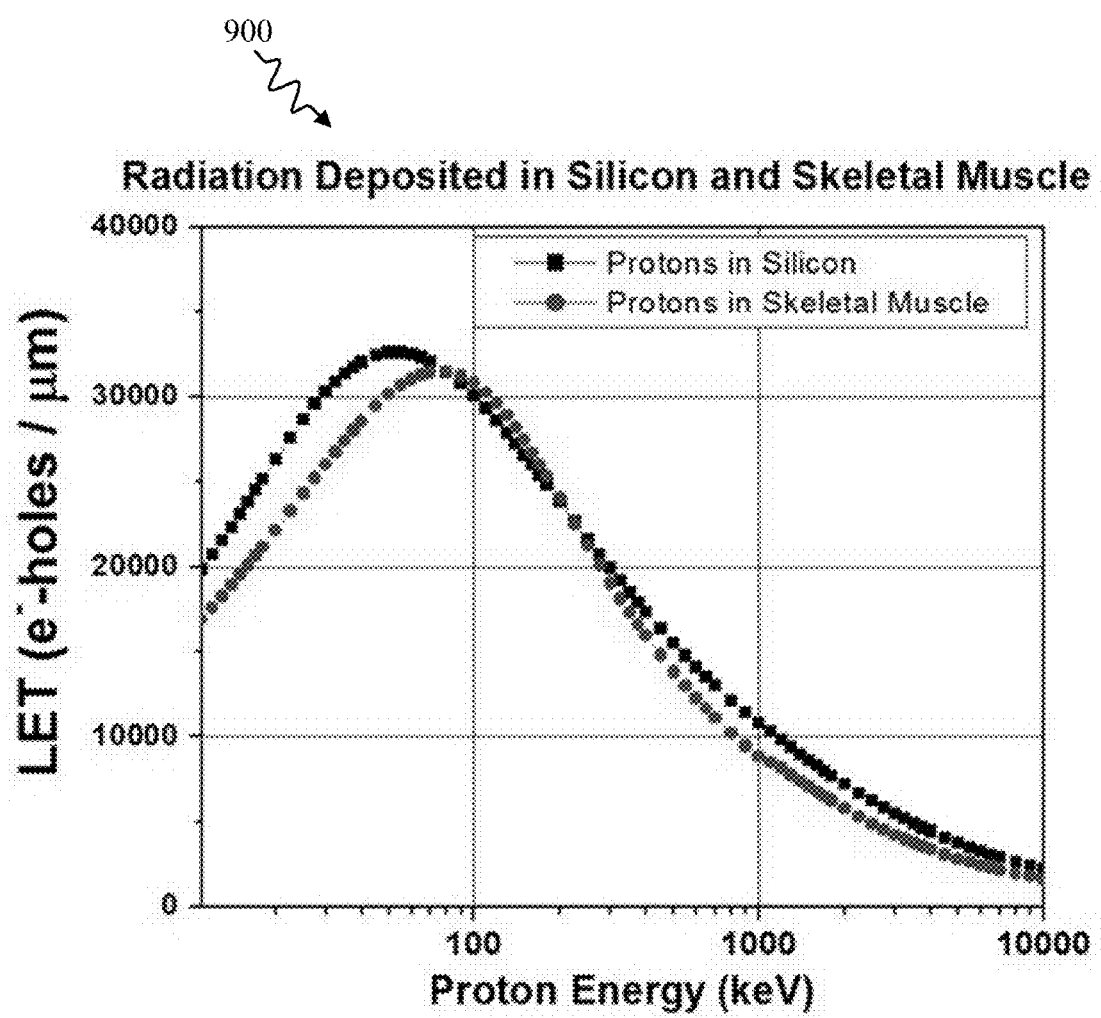
FIG. 9 illustrates an example of an exemplary LET plot that shows the energy loss of protons traveling through silicon and skeletal muscle.

FIG. 9 illustrates an example of an exemplary LET plot 900 that shows the energy loss of protons traveling through silicon and skeletal muscle. The LET plot 900 shown is in units of electron-hole pairs generated per μm of path length. It may be observed that silicon and skeletal muscle have very similar LET value characteristics compared to one another for most proton kinetic energies. For example, for a proton having a kinetic energy of 100 keV, silicon and skeletal muscle have LET values that are within about 5% of each other. Thus, a detector's semiconductor volume fabricated using silicon is a close surrogate for skeletal muscle tissue.

Figure 10:
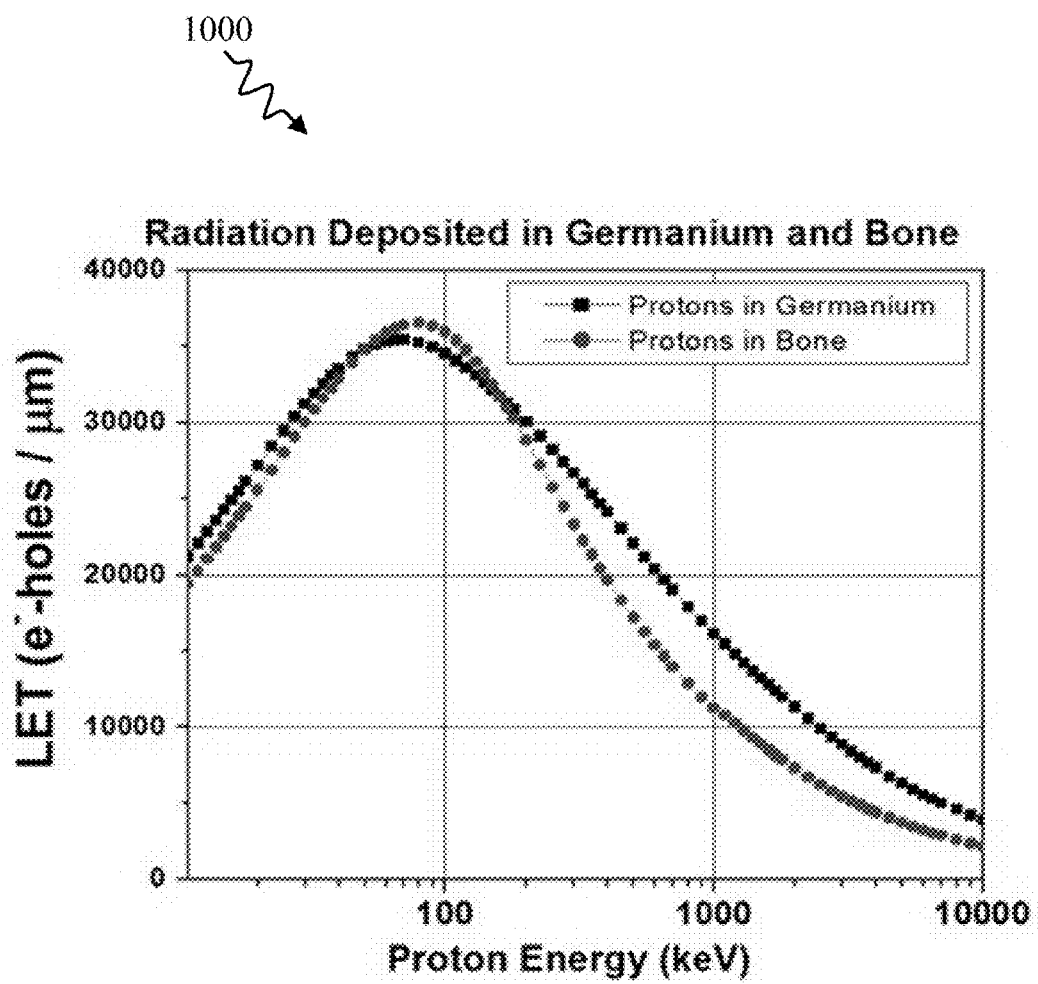
FIG. 10 illustrates an example of an exemplary LET plot that shows the energy loss of protons traveling through germanium and cortical bone.

FIG. 10 illustrates an example of an exemplary LET plot 1000 that shows the energy loss of protons traveling through germanium and cortical bone. The LET plot 1000 shown is in units of electron-hole pairs generated per μm of path length. As described above, it may be observed that germanium and cortical bone have relatively similar LET value characteristics compared to one another for most proton kinetic energies. For example, for a proton having a kinetic energy of 100 keV, germanium and cortical bone have LET values that are within about 5% of each other. Thus, a detector's semiconductor volume fabricated using germanium is a close surrogate for cortical bone tissue.

Semiconductor alloys that combine carbon, silicon, germanium, and other elements provide a myriad of different types material that can be used to fabricate the semiconductor volume of any of the detectors described herein. Thus, any cell or cell component may be mimicked, in part, by selecting a specific semiconductor or combination of semiconductors/elements for a detector's semiconductor volume in order to best match the cell or cell component's LET value characteristics. According to one example, a semiconductor or combination of semiconductors may be used for a detector's semiconductor volume such that the semiconductor volume has an LET plot line that is within +/−5%, +/−10%, +/−15%, +/−20%, +/−25%, +/−30%, +/−35%, +/−40%, +/−45%, or +/−50% of the LET values of the cell type being matched for protons having a kinetic energy between 10 keV and 100,000 keV.

The LET value characteristics in a detector's semiconductor volume may be dependent on many factors, including but not limited to: the atomic number of the atoms in the semiconductor volume; the atomic density of the semiconductor volume; the material conductivity of the semiconductor volume; the lattice structure of the semiconductor volume; and the presence of defects in the semiconductor volume. As such, in addition to the specific semiconductor used for the detector's semiconductor volume, any of the aforementioned factors may be varied in an attempt to mimic the LET value characteristics of a biological tissue, cell, or cell component.

Additional Exemplary Aspects of Microdosimeter

According to the example shown in FIGS. 2-4, the first semiconductor region 202 in the center of the detector 200 is n-type and the second semiconductor region 204 is p-type. However, in other aspects the first semiconductor region 202 may be a heavily doped p-type (i.e., P+ type) semiconductor region and the outer, second semiconductor region 204 may be a heavily doped n-type (i.e., N+ type) semiconductor region. An example of such a detector 1100 is shown in FIGS. 11 and 12.

Figure 11:
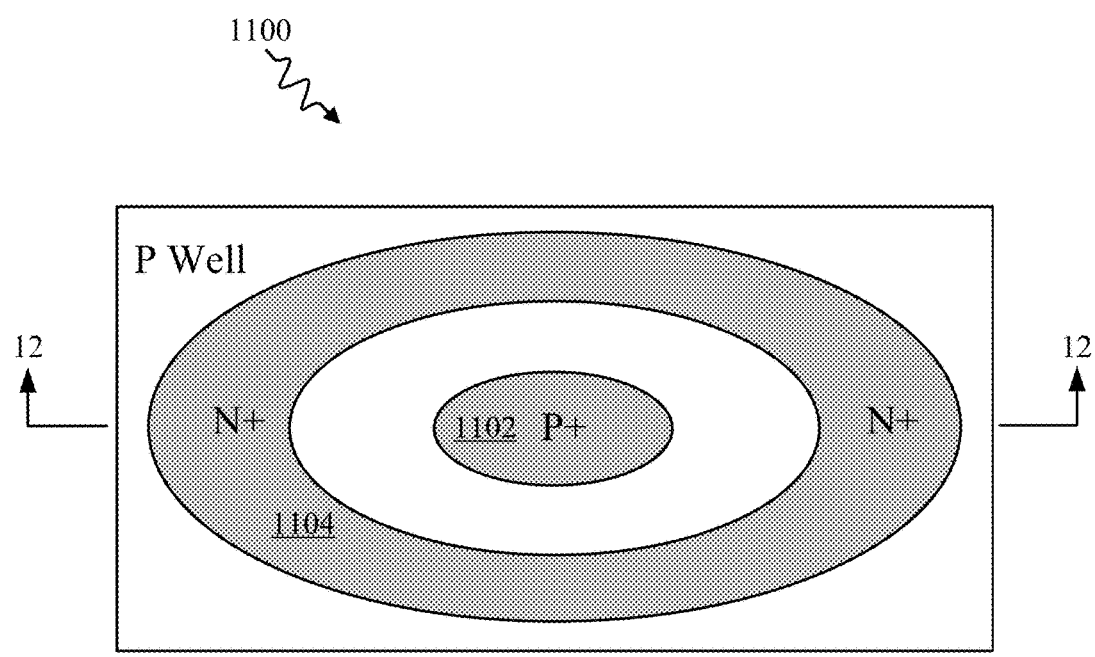
FIG. 11 illustrates a schematic top view of another exemplary detector.
Figure 12:
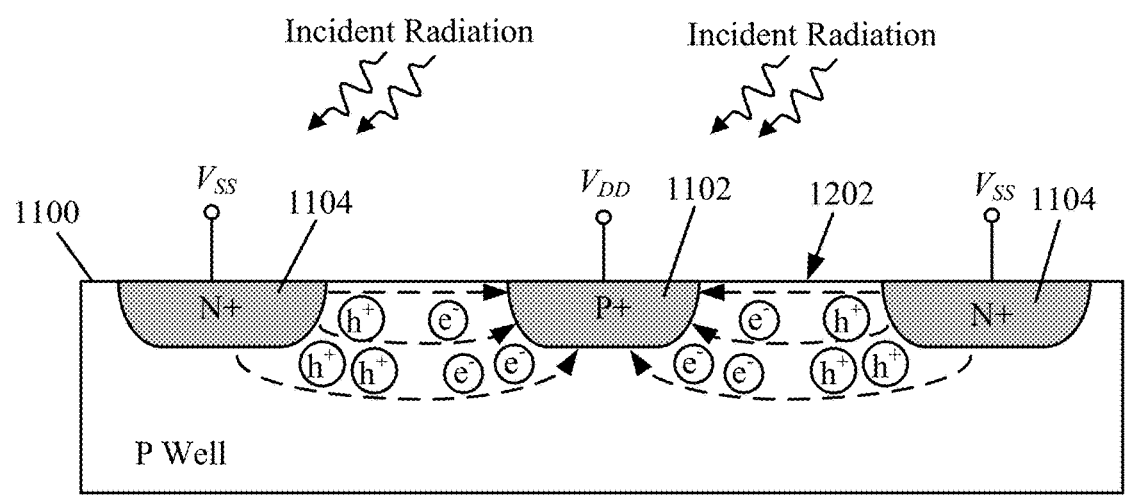
FIG. 12 illustrates a schematic cross-sectional view of the detector shown in FIG. 11.

Specifically, FIG. 11 illustrates a schematic top view of the detector 1100, and FIG. 12 shows a schematic cross-sectional view of the detector 1100 taken along the line 12-12 shown in FIG. 11. Although the first semiconductor region 1102 and second semiconductor region 1104 have a doping type that is reversed with respect to the semiconductor regions 202, 204 of the detector 106, both detectors 106, 1100 may provide substantially similar performance.

The detectors described herein are not limited to any particular shape. For example, the detector 106 shown in FIGS. 2-4 have first and second semiconductor regions 202, 204 that are oval shaped. However, according to other aspects as described in part below, the first and second semiconductor regions 202, 204 may be rectangular, triangular, or have any other shape.

Figure 13:
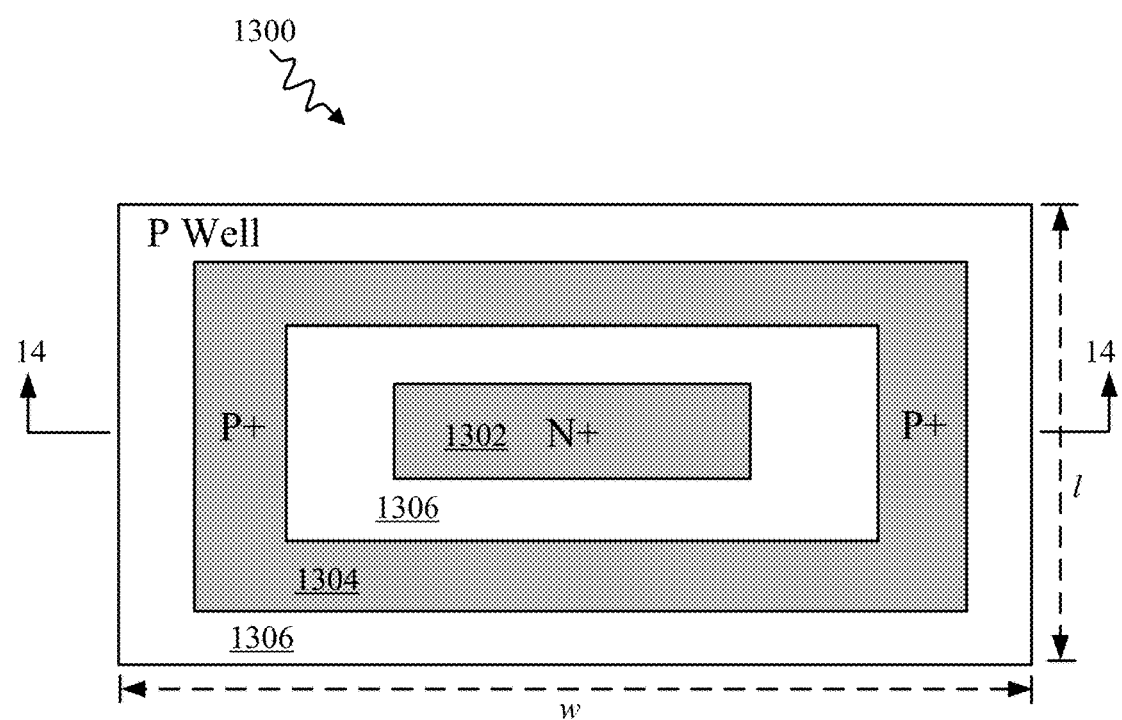
FIG. 13 illustrates a schematic top view of yet another detector.
Figure 14:
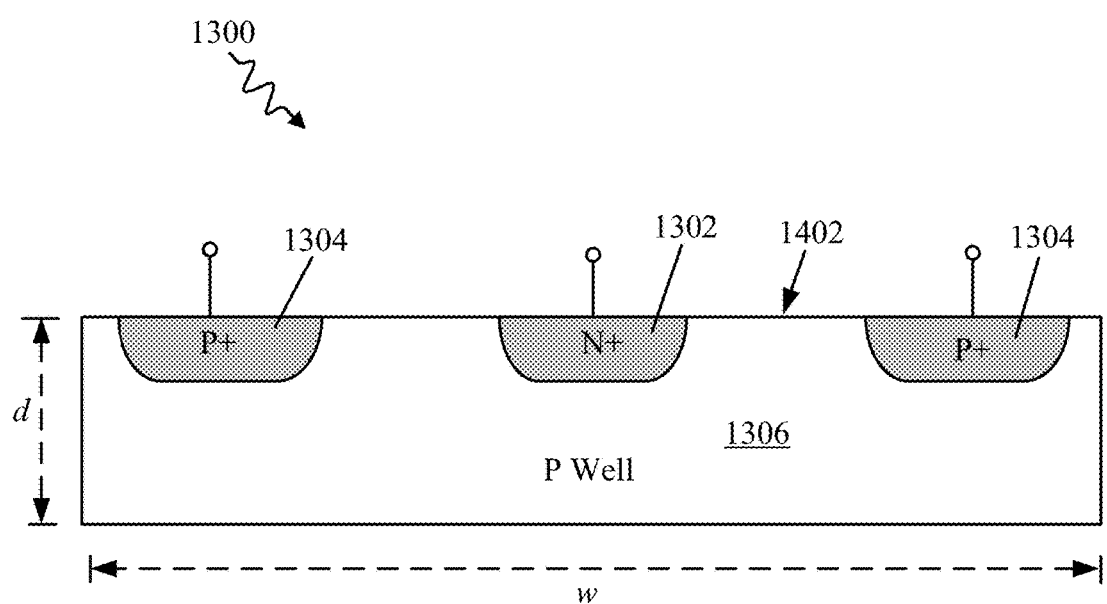
FIG. 14 illustrates a schematic cross-sectional view of the detector shown in FIG. 13.

FIG. 13 illustrates a schematic top view of a detector 1300 according to one aspect. FIG. 14 illustrates a schematic cross-sectional view of the detector 1300 taken along the line 14-14 shown in FIG. 13. Unlike the oval detector 106 shown in FIG. 1, the detector 1300 shown in FIGS. 13 and 14 is rectangular in that the first and second semiconductor regions 1302, 1304 and the p-type well 1306 are concentric rectangles. The detector's semiconductor volume (e.g., p-type well 1306) has a width w, a length l, and a depth d.

In one aspect, the width w and the length l are equal so that the detector 1300 is square cross-section. The detector 1300 operates in the same fashion described above with respect to the detector 106 shown in FIG. 1.

Figure 15:
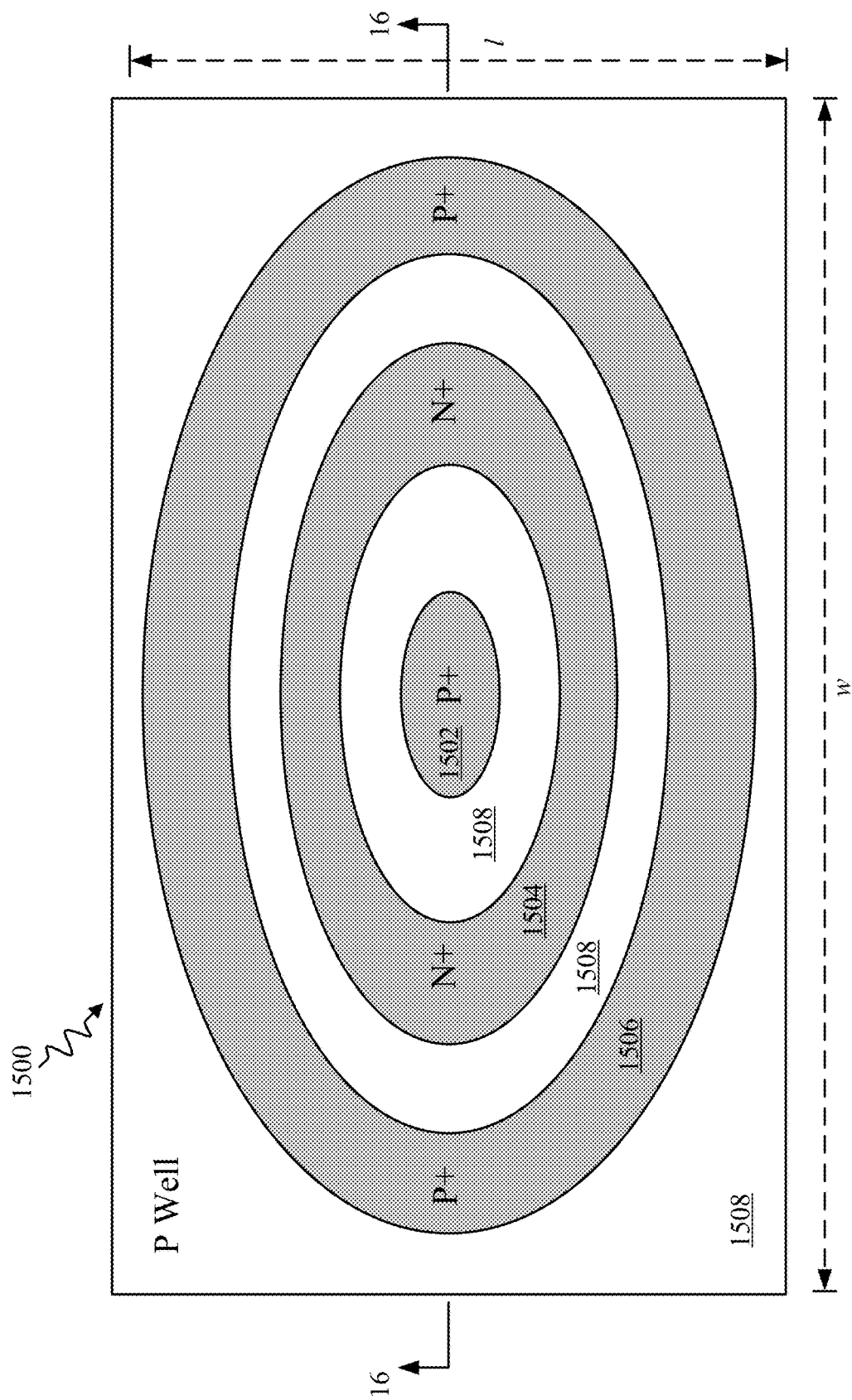
FIG. 15 illustrates a schematic top view of yet another detector.
Figure 16:
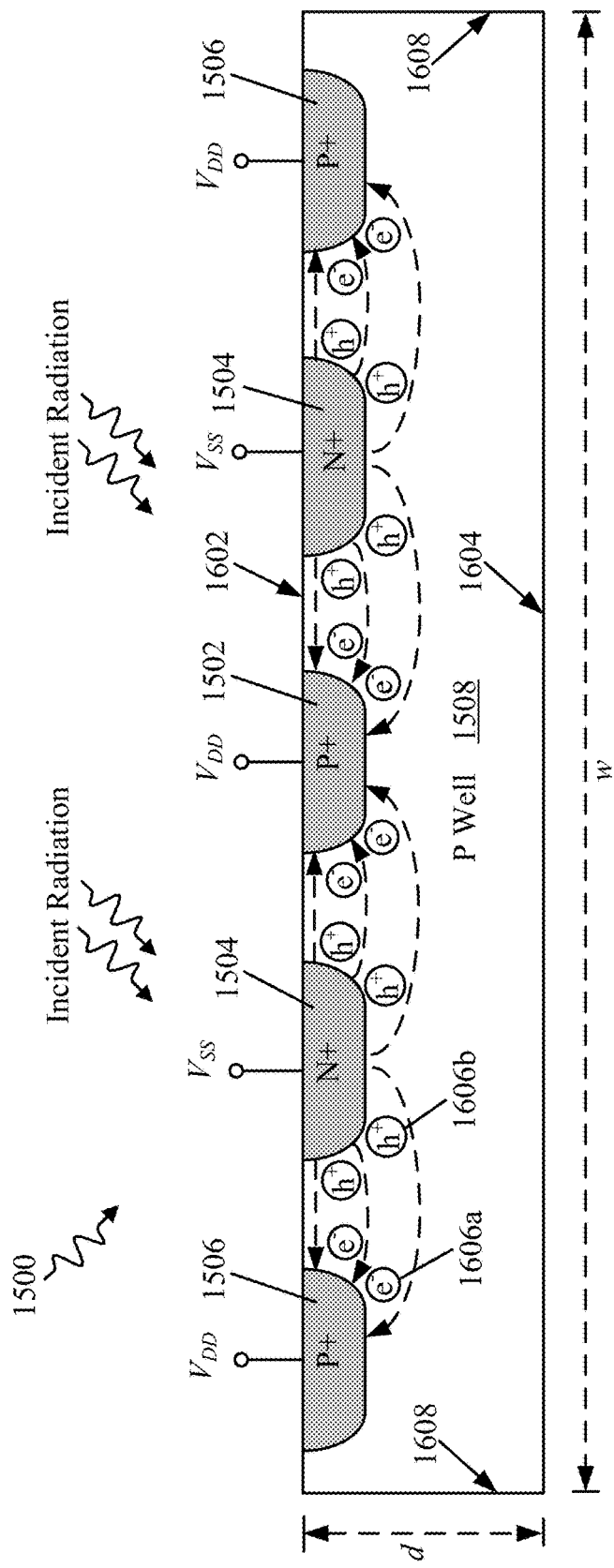
FIG. 16 illustrates a schematic cross-sectional view of the detector shown in FIG. 15.

FIG. 15 illustrates a schematic top view of a radiation detector cell 1500 according to another aspect. FIG. 16 illustrates a schematic cross-sectional view of the detector cell 1500 taken along the line 16-16 of FIG. 15. Referring to FIGS. 15 and 16, the radiation detector cell 1500 is similar to the radiation detector cell 106 of FIGS. 2-4 except that the detector 1500 shown in FIG. 15 includes a third concentric ring-shaped semiconductor region 1506 that surrounds the first and second semiconductor regions 1502, 1504. The first, second, and third semiconductor regions 1502, 1504, 1506 reside within, for example, a p-type well 1508 (e.g., semiconductor volume). The third semiconductor region 1506 has the same doping type as the central, first semiconductor region 1502. In the illustrated example, the first and third semiconductor regions 1502, 1506 are P+ type, and the second semiconductor region 1504 is N+ type. However, in other aspects, the first and third semiconductor regions 1502, 1506 may be N+ type, and the second semiconductor region 1504 may be P+ type.

The detector 1500 operates in a somewhat similar fashion to the detector 106 of FIGS. 2-4. For example, incident radiation generates electron-hole pairs 1606a, 1606b within the semiconductor volume (e.g., p-type well 1508). If the first and third semiconductor regions 1502, 1506 are coupled to the supply voltage $V_{DD}$ and the second semiconductor region 1504 is coupled to ground, an electric field (as illustrated by the dashed arrows) is created within the semiconductor volume 1508 that sweeps the electrons 1606a toward the P+ regions 1502, 1506 and the holes 1606b toward the N+ region 1504. These electrons 1606a and holes 1606b produce a current signal that can be measured and analyzed by a processing circuit (e.g., processing circuit 104 in FIG. 1) to determine the amount of radiation absorbed by the detector 1500.

Notably, the P+ type third semiconductor region 1506 "frames" the detector 1500 such that the electric field generated flows toward both sets of P+ regions 1502, 1506, and any current leakage that may otherwise flow out from the sides 1608 of the detector cell 1500 is reduced. The microdosimeter cell 1500 has a width w, a length l, and a depth d. According to one aspect, the width w and the length l may be equal so that the detector 1500 has a circular cross-section. According to another aspect, the detector 1500 may have a semi-spherical shape such that the first surface (top surface) 1602 is planar (e.g., flat) and the second surface (bottom surface) 1604 is a semi-circular curve (i.e., similar to the detector 600 shown in FIG. 7). According to another aspect, the detector 1500 may be rectangular or square such as the detector 1300 shown in FIGS. 13 and 14.

According to one aspect, the detectors 106, 600, 1100, 1300, 1500 described above may be considered "planar" detectors in that the top surface 302, 702, 1202, 1402, 1602 that is exposed to the ionizing radiation is flat and/or level. According to other aspects the top surface may not be flat but instead have another three dimensional shape, such as a semi-spherical shape (e.g., similar to the second surface 704 in FIG. 7).

Exemplary Radiation Dosimeter

Figure 17:
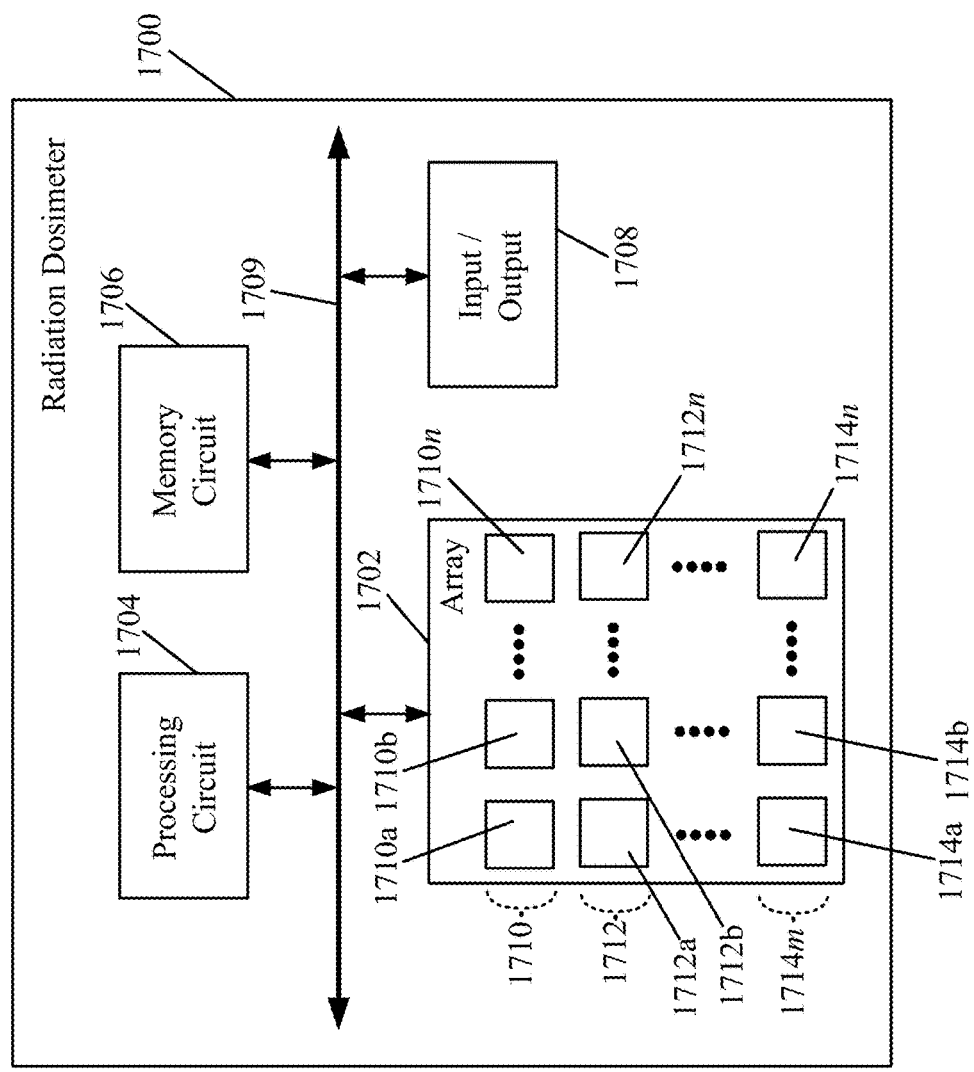
FIG. 17 illustrates a schematic block diagram of another radiation dosimeter.

FIG. 17 illustrates a schematic block diagram of a radiation microdosimeter 1700 according to one aspect. The microdosimeter 1700 comprises a detector cell array 1702, and may further comprise one or more processing circuits 1704, one or more memory circuits 1706, and one or more input/output (I/O) devices 1708. The detector array 1702, the processing circuit 1704, the memory circuit 1706, and the I/O devices 1708 may all communicate with one another via a bus 1709.

Among other things, the processing circuit 1704 (e.g., processor) analyzes signals received from the detector array 1702 to determine the radiation levels detected by the detectors of the detector array 1702. For example, the processing circuit 1702 may be configured to generate a signal based on a plurality of currents generated by a plurality of detectors 1710a, 1710b, . . . 1710n, 1712a, 1712b, . . . 1712n, 1714a, 1714b, . . . 1714n, and the signal generated is indicative of an amount of radiation absorbed by the microdosimeter cell array 1702 and/or the radiation dosimeter 1700. The memory circuit 1706 may include volatile and/or non-volatile memory that stores data and/or algorithms executed by the processing circuit 1704. The I/O device 1708 may include, among other things, a display that indicates the level of radiation detected by the detector array 1702.

According to one aspect, the detector array 1702 includes an integer number m detector cell groupings 1710, 1712, . . . 1714m, where m is an integer greater than or equal to one (1). Each detector grouping includes an integer number n detector cells, where n is an integer greater than or equal to one (1). For example, a first detector grouping 1710 may include detectors 1710a, 1710b, . . . 1710n, a second detector grouping 1712 may include detectors 1712a, 1712b, . . . 1712n, and a third detector grouping may include detectors 1714a, 1714b, . . . 1714n. The detectors 1710a, 1710b, . . . 1710n, 1712a, 1712b, . . . 1712n, 1714a, 1714b, . . . 1714n may be, for example, any one of the detectors 106, 600, 1100, 1300, 1500 shown in FIGS. 2-4, 6, 7, and 11-16. In the example of FIG. 17, there are three detector groupings explicitly shown. However, the detector array 1702 may have any number of detector groupings, and each detector grouping may consist of any number (e.g., one, tens, hundreds, thousands, etc.) of individual detectors.

Each detector grouping 1710, 1712, . . . 1714m may correspond to a particular cell type associated with a biological organism (e.g., a human) that is host to the various types of cell types mimicked by the detector groupings 1710, 1712, . . . 1714m. For example, the first detector grouping 1710 that includes detectors 1710a, 1710b, . . . 1710n may be fabricated to mimic one type of white blood cell of the biological organism, such as neutrophil cell. The second detector grouping 1712 that includes detectors 1712a, 1712b, . . . 1712n may be fabricated to mimic cortical bone cells of the biological organism. The third detector grouping 1714m that includes detectors 1714a, 1714b, . . . 1714n may be fabricated to mimic epithelial cells of the colon of the biological organism. Of course, the detector groupings 1710, 1712, 1714m may include detectors that mimic other type of cells and/or cell components of the biological organism. Each of these detectors 1710a, 1710b, . . . 1710n, 1712a, 1712b, . . . 1712n, 1714a, 1714b, . . . 1714n may be manufactured/designed to imitate properties of the biological cells and/or cell components they correspond to in order to better estimate the radiation absorbed by that particular cell or cell component type, and thus assess the general risk of bodily harm to the biological organism exposed to the radiation event. According to one aspect, the radiation measured/detected at each detector grouping 1710, 1712, . . . 1714m may be separately tabulated and weighted by a relative radiation sensitivity scaling factor of that biological cell type. After weighting the current(s) generated by each detector grouping 1710, 1712, . . . 1714m according to biological cell type, the results are summed to establish the composite radiation exposure for that biological organism represented by the plurality of detector groupings 1710, 1712, . . . 1714m corresponding to the various biological cell types of the organism.

As one example, each detector grouping 1710, 1712, . . . 1714m may correspond to a particular cell component/organelle type of a biological cell. For example, the detectors 1710a, 1710b, . . . 1710n may be designed to mimic a mitochondrion of a neutrophil, the detectors 1712a, 1712b, . . . 1712n may be designed to mimic a nucleus of a neutrophil, and the detectors 1714a, 1714b, . . . 1714n may be designed to mimic a golgi apparatus of a neutrophil. Other cell groupings may each be designed to mimic a other biological cell components/organelles of the neutrophil. According to one aspect, the radiation measured/detected at each detector grouping 1710, 1712, . . . 1714m may be separately tabulated and weighted by a relative radiation sensitivity scaling factor of that biological cell component type. After weighting the current(s) generated by each detector grouping 1710, 1712, . . . 1714m according to biological cell component type, the results are summed to establish the composite radiation exposure for that biological cell represented by the plurality of detector groupings 1710, 1712, . . . 1714m corresponding to the various biological cell component types of the biological cell.

FIG. 18 illustrates a table 1800 that shows exemplary relative radiation sensitivity scaling factors (RRSSF) for various biological cell types associated with a biological organism (e.g., human) according to one aspect of the disclosure. In the example shown, the RRSSF for a neutrophil cell is 0.25, cortical bone cells is 0.05, skeletal muscle is 0.06, and epithelial cells of the colon is 0.28. These values are merely examples, and in practice any value consistent with laboratory experimentation of the actual relative radiation sensitivity of cells of the biological organism based on a specific type of radiation may be used. The RRSSF values may be based on the radiation sensitivity of the one biological cell type relative to (at least) the radiation sensitivity of another biological cell type of the organism. Thus, in the example described above, neutrophil cells are assumed to be five (5) times more sensitive to radiation than cortical bone cells. According to one aspect, the radiation dosimeter's 1700 processing circuit 1704 is configured to generate a signal based on a first current generated at a first detector 1710a and a second current generated at a second detector 1712a. The signal generated may be based on the first current weighted by a first relative radiation sensitivity scaling factor and the second current weighted by a second relative radiation sensitivity scaling factor, where the first relative radiation sensitivity scaling factor is based on radiation sensitivity of the first biological cell type relative to at least radiation sensitivity of the second biological cell type, and the second relative radiation sensitivity scaling factor is based on radiation sensitivity of the second biological cell type relative to at least radiation sensitivity of the first biological cell type.

FIG. 19 illustrates another table 1900 that shows exemplary relative radiation sensitivity scaling factors (RRSSF) for various biological cell component/organelle types associated with a biological cell (e.g., neutrophil cell) according to one aspect of the disclosure. In the example shown, the RRSSF for a mitochondrion is 0.10, a golgi apparatus is 0.08, a nucleus is 0.40, and a specific granule is 0.03. These values are merely examples, and in practice any value consistent with laboratory experimentation of the actual relative radiation sensitivity of the cellular components of the biological cell based on a specific type of radiation may be used. The RRSSF values may be based on the radiation sensitivity of the one biological cell component type relative to (at least) the radiation sensitivity of another biological cell component type of the biological cell. Thus, in the example described above, the cell nucleus is assumed to be five (5) times more sensitive to radiation than the golgi apparatus. According to one aspect, the radiation dosimeter's 1700 processing circuit 1704 is configured to generate a signal based on a first current generated at a first detector 1710*a* and a second current generated at a second detector 1712*a*. The signal generated may be based on the first current weighted by a first relative radiation sensitivity scaling factor and the second current weighted by a second relative radiation sensitivity scaling factor, where the first relative radiation sensitivity scaling factor is based on radiation sensitivity of the first biological cell component type relative to at least radiation sensitivity of the second biological cell component type, and the second relative radiation sensitivity scaling factor is based on radiation sensitivity of the second biological cell component type relative to at least radiation sensitivity of the first biological cell component type.

Referring back to FIG. 17, according to one aspect, each detector within a detector grouping 1710, 1712, . . . 1714*m* may be sized and/or shaped to match the biological cell type or biological cell component to which it corresponds. For example, the detectors 1710*a*, 1710*b*, . . . 1710*n* that correspond to neutrophils may have a width w and length l equal to 13.5 µm, which is approximately the diameter of a neutrophil cell (see e.g., FIG. 5). Similarly, the detector depth d can also be made to correlate with the biological cell or cell component depth. As another example, the detectors 1712*a*, 1712*b*, . . . 1712*n* of the second group 1712 may correspond to the nucleus of the neutrophil and may thus have a device width w, length l, and depth d that is smaller. In other aspects, the detector width w, length l, and/or depth d may be equal to the diameter of the biological cell or cell component being mimicked multiplied by an adjustment factor, for example, between 0.5 and 4.0.

According to one aspect, each detector within a detector group 1710, 1712, . . . 1714*m* may have a semiconductor volume that is composed of a semiconductor material having LET value characteristics that match the LET value characteristics of the biological cell or cell component that detector is attempting to mimic. For example, the semiconductor volumes of the detectors 1710*a*, 1710*b*, . . . 1710*n* may be composed of silicon if the detectors 1710*a*, 1710*b*, . . . 1710*n* are mimicking skeletal muscle cells. Similarly, the semiconductor volumes of the detectors 1710*a*, 1710*b*, . . . 1710*n* may be composed of germanium if the detectors 1710*a*, 1710*b*, . . . 1710*n* are mimicking cortical bone cells.

According to another aspect, silicon may be used as the semiconductor volume regardless of the specific type of biological cell or cell component the detector is trying to mimic in order to save on manufacturing costs and complexity. In such a case, a correction factor may be applied, for example between 0.1 and 3.0 to match the LET characteristics of the silicon semiconductor volume to the biological cell or cell component material being mimicked. In most cases however, the energy deposited by high energy ions in tissue is almost always within a factor of two of that in silicon. An additional correction may also be applied for density changes between that of silicon and the specific biological cell or cell component being mimicked to keep the induced error within a factor of two.

According to one aspect, a possible simplification for some microdosimeters would be to use one detector shape (e.g., a semiconductor volume having a spherical shape (i.e., first surface 302, 702, 1202, 1402, 1602 is curved) or a planar circle, oval, rectangle, etc.) and/or size (e.g., width w, length l, and/or depth d equal to about 1 µm) to mimic the various types of cell granules within a cell. Since granules are believed to be a relatively insensitive component of biological cells, some inaccuracy in approximating the actual radiation absorbed by the granules would not significantly impact an assessment of the comprehensive bodily radiation threat analysis.

According to one aspect, the detectors 106, 600, 1100, 1300, 1500 may be planar as shown in FIGS. 2-4, 6, 7, and 11-16. That is, the semiconductor volumes of these detectors have a flat, planar top surface 302, 702, 1202, 1402, 1602. According to another aspect, detectors may be formed that closely approximate the actual, non-planar shape of the biological cell or cell component they attempt to mimic. For example, the semiconductor volume of a detector may be shaped such that it resembles a red blood cell (e.g., concave or biconcave disk) or a mitochondrion (e.g., capsule shaped) of a neutrophil. As one example, three dimensional (3D) printing processes using a semiconductor (e.g., silicon, carbon, germanium, etc.) as a deposition material may be used to form the non-planar detectors having the biological cell or cell component-specific shapes, such as, but not limited to ovals, spheres, rods, triangular prisms, rectangular prisms, etc. Such detectors may have a polycrystalline semiconductor volume. However, according to some applications planar detectors 106, 600, 1100, 1300, 1500 may be preferred due to manufacturing ease and budgetary constraints.

According to another aspect, the semiconductor material comprising the semiconductor volume of the detectors 106, 600, 1100, 1300, 1500 may be doped with various elements (e.g., phosphorus if the semiconductor volume is n-type, or boron if the semiconductor volume is p-type) to various degrees in order to replicate the conductivity of the biological cell or cell component that the detector 106, 600, 1100, 1300, 1500 is attempting to mimic. As discussed above, silicon may be doped to change its conductivity by over six orders of magnitude. For example, single-crystal silicon doped with phosphorus to a level of $10^{12}/cm^3$ may have a resistivity of approximately 25,000 Ω-cm, which can be used to mimic the resistivity of biological cells or cell components that are as conductive as insulators (e.g., cortical bone cells). By contrast, doping the single-crystal silicon to $10^{19}/cm^3$ may provide a resistivity of about 0.01 Ω-cm, which may be used to mimic biological cells or cell components that are as conductive as common conductors (e.g., biological cell or cell components that are predominantly saline). A vast majority of cells, cell components, and tissues lie within this range of conductivity.

According to another aspect, the semiconductor material comprising the semiconductor volume of the detectors 106, 600, 1100, 1300, 1500 may use a specific type of semiconductor to further approximate the radiation absorption characteristics (e.g., LET characteristics) of the biological cell or cell component that the detector 106, 600, 1100, 1300, 1500 is attempting to mimic. For example, a high band-gap semiconductor may be used for insulating cells such as bone, and low band-gap semiconductors may be used for conducting cells such as gastro-intestinal cells.

According to yet another aspect, a detector grouping 1710, 1712, . . . 1714*m* that mimics biological cells that are near the body's surface (e.g., cells underneath the skin) may be covered with a radiation absorption layer, such as a few millimeters of polyethylene or another hydrocarbon, in order to mimic the radiation absorption properties of skin.

According to another aspect, the detectors 106, 600, 1100, 1300, 1500 may be encased or covered by a tissue equivalent medium to better approximate the radiation reaching the biological cell or cell component that the detector array 1702 mimics. The tissue equivalent medium generates secondary charged particles that may also be detected and measured by the semiconductor volumes of the detectors 106, 600, 1100, 1300, 1500.

Thus, according to one aspect, the radiation dosimeter 1700 comprises a microdosimeter cell array 1702 including a first microdosimeter cell 1710a having a first semiconductor volume (e.g., any of the semiconductor volumes 206, 606, 1306, 1508 described above) configured to generate a first current in response to incident radiation. The first semiconductor volume may have at least one of a first size, a first shape, a first semiconductor type, and/or a first semiconductor doping type and concentration that is associated with a first biological cell type or a first biological cell component type. The radiation dosimeter further comprises a processing circuit 1704 communicatively coupled to the microdosimeter cell array 1702 and configured to generate a signal based on the first current, where the signal is indicative of an amount of radiation absorbed by the microdosimeter cell array 1702.

The microdosimeter cell array 1702 may further include a second microdosimeter cell 1712a that has a second semiconductor volume (e.g., any of the semiconductor volumes 206, 606, 1306, 1508 described above) configured to generate a second current in response to the incident radiation. The second semiconductor volume may have at least one of a second size, a second shape, a second semiconductor type, and/or a second semiconductor doping type and concentration that is associated with a second biological cell type or a second biological cell component type, and where and at least one of (a) the first size is different than the second size, (b) the first shape is different than the second shape, (c) the first semiconductor type is different than the second semiconductor type, and/or (d) the first semiconductor doping type and concentration is different than the second semiconductor doping type and concentration. The signal generated by the processing circuit may be further based on the second current.

The microdosimeter cell array 1702 may further include a third microdosimeter cell having a third semiconductor volume (e.g., any of the semiconductor volumes 206, 606, 1306, 1508 described above) configured to generate a third current in response to the incident radiation. The third semiconductor volume may have at least one of a third size, a third shape, a third semiconductor type, and/or a third semiconductor doping type and concentration that is associated with a third biological cell type or a third biological cell component type, and where at least one of (a) the second size is different than the third size, (b) the second shape is different than the third shape, (c) the second semiconductor type is different than the third semiconductor type, and/or (d) the second semiconductor doping type and concentration is different than the third semiconductor doping type and concentration. The signal generated by the processing circuit may be further based on the third current.

According to another aspect, the radiation dosimeter 1700 comprises a first microdosimeter cell 1710a that includes a first semiconductor volume (e.g., any of the semiconductor volumes 206, 606, 1306, 1508 described above), a first cell first semiconductor region (e.g., any of the first semiconductor regions 202, 602, 1102, 1302, 1502 described above), and a first cell second semiconductor region (e.g., any of the second semiconductor regions 204, 604, 1104, 1304, 1504 described above). The first semiconductor volume may be configured to generate a first current in response to radiation incident upon the radiation dosimeter, where the first current is configured to flow between the first cell first semiconductor region and the first cell second semiconductor region. The first microdosimeter cell may include a first size, a first semiconductor type, and/or a first semiconductor doping type and concentration that is based on a first biological cell type or a first biological cell organelle type. The radiation dosimeter 1700 may further comprise a processing circuit 1704 communicatively coupled to the first microdosimeter cell 1710a and configured to generate a signal based on the first current. The signal may be indicative an amount of the radiation absorbed the radiation dosimeter. The dosimeter 1700 may further comprise a display 1710 communicatively coupled to the processing circuit and configured to display a radiation level reading based on the signal generated.

The radiation dosimeter 1700 may further comprise a second microdosimeter cell 1712a including a second semiconductor volume (e.g., any of the semiconductor volumes 206, 606, 1306, 1508 described above), a second cell first semiconductor region (e.g., any of the first semiconductor regions 202, 602, 1102, 1302, 1502 described above), and a second cell second semiconductor region (e.g., any of the second semiconductor regions 204, 604, 1104, 1304, 1504 described above). The second semiconductor volume may be configured to generate a second current in response to the radiation incident upon the radiation dosimeter, and the second current is configured to flow between the second cell first semiconductor region and the second cell second semiconductor region. The second microdosimeter cell includes a second size, a second semiconductor type, and/or a second semiconductor doping type and concentration that is based on a second biological cell type or a second biological cell organelle type, and at least one of (a) the first size is different than the second size, (b) the first semiconductor type is different than the second semiconductor type, and/or (c) the first semiconductor doping type and concentration is different than the second semiconductor doping type and concentration, and wherein the signal generated by the processing circuit is further based on the second current.

Exemplary Method

Figure 20:
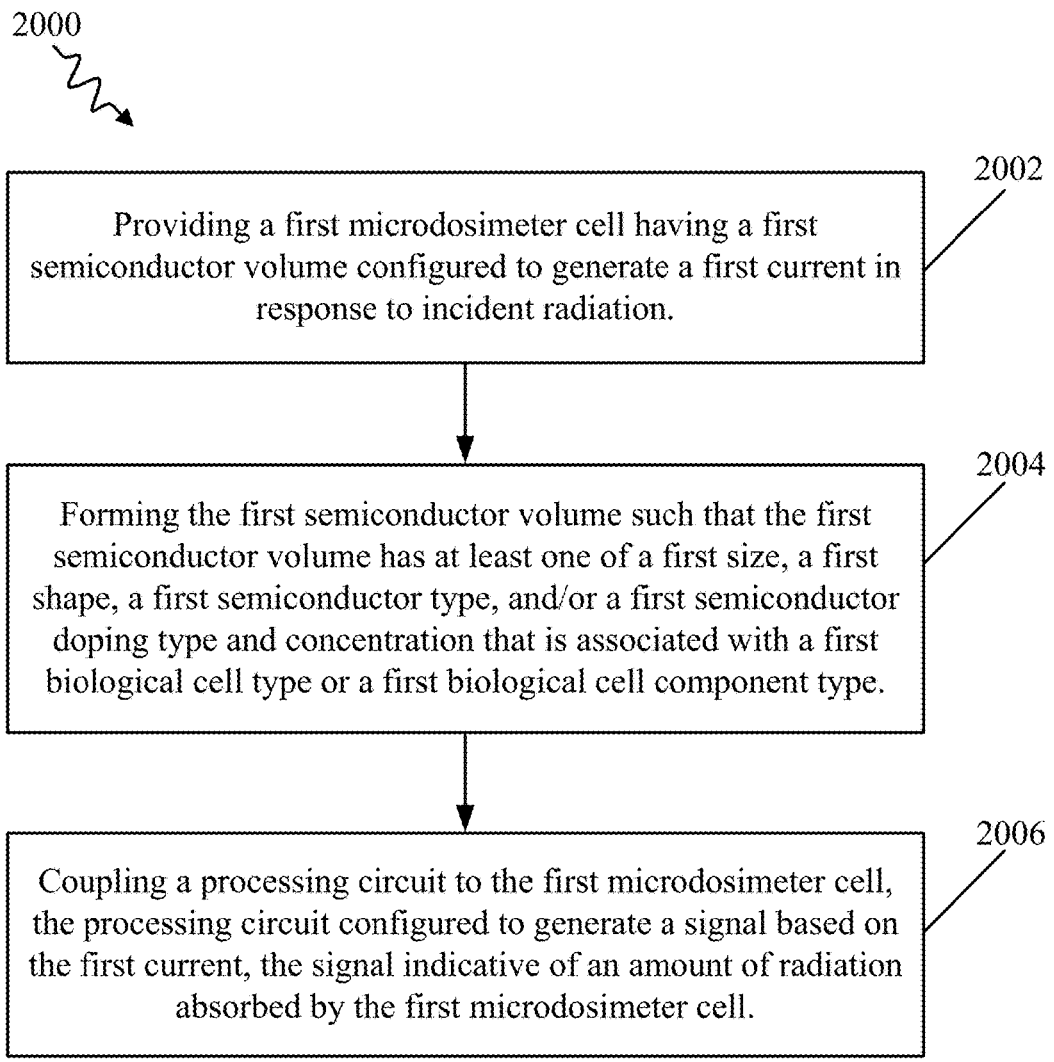
FIG. 20 illustrates a flow chart of an exemplary method.

FIG. 20 illustrates a flow chart 2000 of an exemplary method according to one aspect of the disclosure. First, a first microdosimeter cell is provided having a first semiconductor volume configured to generate a first current in response to incident radiation 2002. Next, the first semiconductor volume is formed such that the first semiconductor volume has at least one of a first size, a first shape, a first semiconductor type, and/or a first semiconductor doping type and concentration that is associated with a first biological cell type or a first biological cell component type 2004. Then, a processing circuit is coupled to the first microdosimeter cell, where the processing circuit is configured to generate a signal based on the first current, and the signal is indicative of an amount of radiation absorbed by the first microdosimeter cell 2006.

According to one aspect, the method further comprises: providing a second microdosimeter cell having a second semiconductor volume configured to generate a second current in response to the incident radiation; forming the second semiconductor volume such that the second semiconductor volume has at least one of a second size, a second shape, a second semiconductor type, and/or a second semiconductor doping type and concentration that is associated with a second biological cell type or a second biological cell component type, and at least one of (a) the first size is different than the second size, (b) the first shape is different than the second shape, (c) the first semiconductor type is different than the second semiconductor type, and/or (d) the first semiconductor doping type and concentration is different than the second semiconductor doping type and concentration; and coupling the second microdosimeter cell to the processing circuit, the processing circuit further configured to generate the signal also based on the second current, the signal indicative of an amount of radiation absorbed by the first and second microdosimeter cells.

One or more of the components, steps, features, and/or functions illustrated in FIGS. 1, 2, 3, 4, 5, 6, 7, 8, 9, 10, 11, 12, 13, 14, 15, 16, 17, 18, 19, and/or 20 may be rearranged and/or combined into a single component, step, feature or function or embodied in several components, steps, or functions. Additional elements, components, steps, and/or functions may also be added without departing from the invention.

Also, it is noted that the aspects of the present disclosure may be described as a process that is depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the invention described herein can be implemented in different systems without departing from the invention. It should be noted that the foregoing aspects of the disclosure are merely examples and are not to be construed as limiting the invention. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

What is claimed is:

1. A method of manufacturing a radiation microdosimeter, the method comprising:
    identifying a first biological cell type;
    determining at least one of a size of the first biological cell type, a shape of the first biological cell type, a conductivity of the first biological cell type, and/or a linear energy transfer (LET) value of the first biological cell type for a first type of radiation;
    forming a first microdosimeter cell to have a first semiconductor volume made of semiconductor material, the first semiconductor volume configured to generate a first current in response to incident radiation, the first semiconductor volume formed to have at least one of (a) a first size approximating the determined size of the first biological cell type, (b) a first shape approximating the determined shape of the first biological cell type, (c) a first semiconductor doping type and concentration having a conductivity that approximates the determined conductivity of the first biological cell type, and/or (d) a first semiconductor type having an LET value for the first type of radiation that approximates the determined LET value of the first biological cell type for the first type of radiation; and
    communicatively coupling a processing circuit to the first microdosimeter cell, the processing circuit configured to generate a signal value proportional to the first current generated by the first semiconductor volume, the signal value indicative of an amount of radiation absorbed by the first semiconductor volume.

2. The method of claim 1, further comprising:
    determining at least one of the conductivity of the first biological cell type and/or the LET value of the first biological cell type for the first type of radiation, and wherein the first semiconductor volume is formed to have at least one of the first semiconductor doping type and concentration having the conductivity that approximates the determined conductivity of the first biological cell type and/or the first semiconductor type having the LET value for the first type of radiation that approximates the determined LET value of the first biological cell type for the first type of radiation.

3. The method of claim 1, further comprising:
    forming a microdosimeter cell array having a plurality of microdosimeter cells, the plurality of microdosimeter cells including the first microdosimeter cell.

4. The method of claim 3, further comprising:
    identifying a second biological cell type that is different than the first biological cell type;
    determining at least one of a size of the second biological cell type, a shape of the second biological cell type, a conductivity of the second biological cell type, and/or a linear energy transfer (LET) value of the second biological cell type for a second type of radiation; and
    forming a second microdosimeter cell of the plurality of microdosimeter cells to have a second semiconductor volume made of semiconductor material, the second semiconductor volume configured to generate a second current in response to incident radiation, the second semiconductor volume formed to have at least one of (a) a second size approximating the determined size of the second biological cell type, the second size different than the first size, (b) a second shape approximating the determined shape of the second biological cell type, the second shape different than the first shape, (c) a second semiconductor doping type and concentration having a conductivity that approximates the determined conductivity of the second biological cell type, the second semiconductor doping type and concentration different than the first semiconductor doping type and concentration, and/or (d) a second semiconductor type having an LET value for the second type of radiation that approximates the determined LET value of the second biological cell type for the second type of radiation, the second semiconductor type different than the first semiconductor type.

5. The method of claim 4, further comprising:
    communicatively coupling the processing circuit to the second microdosimeter cell, the signal value generated by the processing circuit proportional to the first current and the second current, the signal value indicative of an amount of radiation absorbed by the first semiconductor volume and the second semiconductor volume.

6. The method of claim 1, further comprising:
    determining an average diameter of the first biological cell type; and
    forming the first semiconductor volume to have a width w that approximates the determined average diameter of the first biological cell type.

7. The method of claim 1, wherein the first type of radiation includes protons having a kinetic energy between 10 kilo-electron-volts (keV) and 100,000 keV, and the method further comprises:
- determining the LET value of the first biological cell type for the first type of radiation;
- selecting the first semiconductor type of the first microdosimeter cell to have an LET value for the first type of radiation that approximates the determined LET value of the first biological cell type for the first type of radiation; and
- forming the first microdosimeter cell to have the first semiconductor volume with the first semiconductor type.

8. The method of claim 1, the method further comprising:
- determining the conductivity of the first biological cell type;
- selecting the first semiconductor doping type and concentration of the first microdosimeter cell to have a conductivity that approximates the determined conductivity of the first biological cell type; and
- forming the first microdosimeter cell to have the first semiconductor volume with the first semiconductor doping type and concentration.

9. The method of claim 1, wherein the first biological cell type is one of a neutrophil cell, an eye lens epithelial cell, a colon epithelial cell, a cortical bone cell, an intestinal crypt cell, a myelocyte cell, a lymphocyte cell, a spermatogonia cell, or an erythroblast cell.

10. The method of claim 1, wherein the first biological cell type is an eye lens epithelial cell.

11. The method of claim 1, further comprising:
- forming the first semiconductor volume to have the first size approximate the determined size of the first biological cell type;
- identifying a second biological cell;
- determining a size of the second biological cell;
- forming a second microdosimeter cell to have a second semiconductor volume made of semiconductor material, the second semiconductor volume configured to generate a second current in response to incident radiation, the second semiconductor volume formed to have a second size approximating the determined size of the second biological cell, the second size different than the first size; and
- communicatively coupling the processing circuit to the second microdosimeter cell, the signal value generated by the processing circuit proportional to the first current and the second current, the signal value indicative of an amount of radiation absorbed by the first semiconductor volume and the second semiconductor volume.

12. A method of manufacturing a radiation microdosimeter, the method comprising:
- identifying a first biological cell component type;
- determining at least one of a size of the first biological cell component type, a shape of the first biological cell component type, a conductivity of the first biological cell component type, and/or a linear energy transfer (LET) value of the first biological cell component type for a first type of radiation;
- forming a first microdosimeter cell to have a first semiconductor volume made of semiconductor material, the first semiconductor volume configured to generate a first current in response to incident radiation, the first semiconductor volume formed to have at least one of (a) a first size approximating the determined size of the first biological cell component type, (b) a first shape approximating the determined shape of the first biological cell component type, (c) a first semiconductor doping type and concentration having a conductivity that approximates the determined conductivity of the first biological cell component type, and/or (d) a first semiconductor type having an LET value for the first type of radiation that approximates the determined LET value of the first biological cell component type for the first type of radiation;
- providing a processing circuit configured to generate a signal value proportional to the first current, the signal value indicative of an amount of radiation absorbed by the first microdosimeter cell; and
- communicatively coupling the processing circuit to the first microdosimeter cell.

13. The method of claim 12, further comprising:
- forming a microdosimeter cell array having a plurality of microdosimeter cells, the plurality of microdosimeter cells including the first microdosimeter cell and a second microdosimeter cell;
- identifying a second biological cell component type that is different than the first biological cell component type;
- determining at least one of a size of the second biological cell component type, a shape of the second biological cell component type, a conductivity of the second biological cell component type, and/or a linear energy transfer (LET) value of the second biological cell component type for a second type of radiation; and
- forming the second microdosimeter cell of the plurality of microdosimeter cells to have a second semiconductor volume made of semiconductor material, the second semiconductor volume configured to generate a second current in response to incident radiation, the second semiconductor volume formed to have at least one of (a) a second size approximating the determined size of the second biological cell component type, the second size different than the first size, (b) a second shape approximating the determined shape of the second biological cell component type, the second shape different than the first shape, (c) a second semiconductor doping type and concentration having a conductivity that approximates the determined conductivity of the second biological cell component type, the second semiconductor doping type and concentration different than the first semiconductor doping type and concentration, and/or (d) a second semiconductor type having an LET value for the second type of radiation that approximates the determined LET value of the second biological cell component type for the second type of radiation, the second semiconductor type different than the first semiconductor type, and wherein the processing circuit is communicatively coupled to the second microdosimeter cell and further configured to generate a signal value proportional to the first current and the second current, the signal value indicative of an amount of radiation absorbed by the first microdosimeter cell and the second microdosimeter cell.

14. The method of claim 12, wherein the first biological cell component type is one of a nucleus, a golgi apparatus, a specific granule, an azurophil granule, or a mitochondrion.

15. A method of manufacturing a radiation microdosimeter, the method comprising:
- identifying a first biological cell;
- determining a size of the first biological cell, a conductivity of the first biological cell, and a linear energy transfer (LET) value of the first biological cell for a first type of radiation; and
- forming a first microdosimeter cell array that includes a first plurality of microdosimeter cells each having a semiconductor volume adapted to generate a first current in response to incident radiation, the semiconductor volumes of each of the first plurality of microdosimeter cells formed to have (a) a first size approximating the determined size of the first biological cell, (b) a first semiconductor doping type and concentration having a conductivity that approximates the determined conductivity of the first biological cell, and (c) a first semiconductor type having an LET value for the first type of radiation that approximates the determined LET value of the first biological cell for the first type of radiation.

16. The method of claim 15, further comprising:
providing a processing circuit configured to generate a signal value proportional to the first current of the first plurality of microdosimeter cells, the signal value indicative of an amount of radiation absorbed by the first microdosimeter cell array; and
communicatively coupling the processing circuit to the first microdosimeter cell array.

17. The method of claim 16, further comprising:
providing a display; and
communicatively coupling the display to the processing circuit, the display adapted to display a reading based on the signal value generated by the processing circuit.

18. The method of claim 16, further comprising:
identifying a second biological cell;
determining a size of the second biological cell, a conductivity of the second biological cell, and a linear energy transfer (LET) value of the second biological cell for the first type of radiation;
forming a second microdosimeter cell array that includes a second plurality of microdosimeter cells each having a semiconductor volume adapted to generate a second current in response to incident radiation, the semiconductor volumes of each of the second plurality of microdosimeter cells formed to have (a) a second size approximating the determined size of the second biological cell, (b) a second semiconductor doping type and concentration having a conductivity that approximates the determined conductivity of the second biological cell, and (c) a second semiconductor type having an LET value for the first type of radiation that approximates the determined LET value of the second biological cell for the first type of radiation, wherein the processing circuit is further configured to generate the signal value proportional to the first current of the first plurality of microdosimeter cells and the second current of the second plurality of microdosimeter cells, the signal value indicative of an amount of radiation absorbed by the first and second microdosimeter cell arrays.

19. The method of claim 15, further comprising:
determining an average diameter of the first biological cell; and
forming the first semiconductor volume to have a width w that approximates the determined average diameter of the first biological cell.

20. The method of claim 15, wherein the first biological cell is one of a neutrophil cell, an eye lens epithelial cell, a colon epithelial cell, a cortical bone cell, an intestinal crypt cell, a myelocyte cell, a lymphocyte cell, a spermatogonia cell, or an erythroblast cell.

* * * * *